US006083753A

United States Patent [19]
Kelly et al.

[11] Patent Number: 6,083,753
[45] Date of Patent: *Jul. 4, 2000

[54] SOLUBLE HUMAN PROLACTIN RECEPTORS

[75] Inventors: Paul A. Kelly, Paris, France; Makoto Nagano, Philadelphia, Pa.

[73] Assignees: Inserm, Paris, France; Applied Research Systems ARS Holding N.V., Curacao, Netherlands Antilles

[*] Notice: This patent issued on a continued prosecution application filed under 37 CFR 1.53(d), and is subject to the twenty year patent term provisions of 35 U.S.C. 154(a)(2).

[21] Appl. No.: 08/970,428

[22] Filed: Nov. 14, 1997

Related U.S. Application Data

[62] Division of application No. 08/806,597, Feb. 26, 1997
[60] Provisional application No. 60/012,503, Feb. 29, 1996.

[51] Int. Cl.[7] .................................................. C12N 15/00
[52] U.S. Cl. ...................... 435/691; 435/71.1; 435/320.1; 435/325; 435/252.3; 435/254.11; 536/23.5; 536/23.1; 530/350
[58] Field of Search .................................. 435/69.1, 71.1, 435/320.1, 325, 252.3, 254.11, 69.8; 536/23.5, 23.1, 23.51; 530/350; 930/300

[56] References Cited

U.S. PATENT DOCUMENTS

| | | |
|---|---|---|
| 4,992,378 | 2/1991 | Kelly et al. . |
| 5,605,885 | 2/1997 | Bernton et al. . |

OTHER PUBLICATIONS

Jean–Marie Boutin et al., Cloning and Expression of the Rat Prolactin Receptor, a Member of the Growth Hormone/Prolactin Receptor Gene Family, *Cell*, vol. 53, 69–77, 1988.

Jean–Marie Boutin et al., Identification of a cDNA Encoding a Long Form of Prolactin Receptor in Human Hepatoma and Breast Cancer Cells, *Molecular Endocrinology*, vol. 3, No. 9, 1455–1461, 1989.

Brian C. Cunningham et al., Zinc Mediation of the Binding of Human Growth Hormone to the Human Prolactin Receptor, *Science*, vol. 250, 1709–1712, 1990.

Nazario Esposito et al., Expression of Two Isoforms of the Human Growth Hormone Receptor in Normal Liver and Hepatocarcinoma, *Molecular and Cellular Endocrinology*, 103, 13–20, 1994.

Germaine FUH and James A. Wells, Prolactin Receptor Antagonists That Inhibit the Growth of Breast Cancer Cell Lines, *The Journal of Biological Chemistry*, vol. 270, No. 22, 13133–13137, 1995.

Paul A. Kelly et al., The Growth Hormone/Prolactin Receptor Family, *Recent Progress in Hormone Research*, vol. 48, pp. 123–164, 1993.

Laurence Lesueur et al., Roles of Extracellular and Cytoplasmic Domains of the Prolactin Receptor in Signal Transduction to Milk Protein Genes, *Molecular Endocrinology*, vol. 7, No. 9, 1178–1184, 1993.

David W. Leung et al., Growth Hormone Receptor and Serum Binding Protein: Purification, Cloning and Expression, *Nature*, vol. 330, 537–543, Dec. 1987.

P. E. Lobie et al., Prolactin Receptor Expression in the Gastrointestinal Tract: Characterization of the Prolactin Receptor of Gastric Mucosa, *Journal of Endocrinology*, 139, 371–382, 1993.

Isabelle Pellegrini et al., Expression of Prolactin and Its Receptor in Human Lymphoid Cells, *Molecular Endocrinology*, vol. 6, No. 7, 1023–1031, 1992.

Maria Rozakis–Adcock and Paul A. Kelly, Identification of Ligand Binding Determinants of the Prolactin Receptor, *The Journal of Biological Chemistry*, vol. 267, No. 11, 7428–7433, 1992.

Maria Rozakis–Adcock and Paul A. Kelly, Mutational Analysis of the Ligand–Binding Domain of the Prolactin Receptor, *The Journal of Biological Chemistry*, vol. 266, No. 25, 16472–16477, 1991.

Margrit Urbanek et al., Functional Characterization of the Alternatively Spliced, Placental Human Growth Hormone Receptor, *The Journal of Biological Chemistry*, vol. 268, 19025–19032, Sep. 1993.

*Primary Examiner*—Lorraine Spector
*Assistant Examiner*—Eliane Lazar-Wesley
*Attorney, Agent, or Firm*—Browdy and Neimark

[57] ABSTRACT

Soluble polypeptides of human prolactin receptor, corresponding to products expressed from differentially spliced mRNA and obtainable from various human tissues, are reported and recombinant molecules containing nucleic acid sequences encoding the soluble polypeptides of human prolactin receptor can be constructed and inserted into expression vectors for production in transformed host cells.

16 Claims, 6 Drawing Sheets

FIG. 4B

| | PCR Fragment Size | Missing Exon | Frame Shift | Size of Putative Protein | Suspected Form | Cysteine | Sugar | WS motif |
|---|---|---|---|---|---|---|---|---|
| A | 524bp | 4 | + | 11aa | secreted | (C3) | 0 | – |
| B | 315bp | 5, 6 | + | 94aa | secreted | C1, 2 | N1, (N3) | – |
| C | 353bp | 4, 5 | – | 498aa | anchored | C5 | N3 | + |
| D | 330bp | (4), 5, (6) | + | 24aa | secreted | C1 | 0 | – |
| E | 496bp | 6 | + | 110aa | secreted | C1-4, (5) | N1, 2 | – |
| F | 478bp | (10) | + | 325aa | anchored | C15 | N1-3 | + |

FIG. 5

```
Clone A:          70  204
          --- --- CTT CTG AAT G/AG AGA CAC TCA ---
          --- --- Leu Leu Asn Glu  Arg His Ser ---

Clone B:         203  544
          --- --- CAC AGG GAA GG/A TCC ATT TTG ---
          --- --- His Arg Glu Gly  Ser Ile Leu ---

Clone C:          70  374
          --- --- CTT CTG AAT G/TT CAG CCA GAC ---
          --- --- Leu Leu Asn Val  Gln Pro Asp ---

Clone D:         135  462
          --- --- ACA TTC ACC/TAC CCT GAT ---
          --- --- Thr Phe Thr Tyr  Pro Asp ---

Clone E:         373  544
          --- --- ACT TAC ATA G/AT CCA TTT TGC ---
          --- --- Thr Tyr Ile Asp  Pro Phe Cys ---

Clone F:
          --- --- CCA AGT CAA G/AG AGA GAA ------------------------------ TGA
          --- --- Pro Ser Gln Glu  Arg Glu Gln Arg Gln Glu Ala Arg Asp Ser
```

SOLUBLE HUMAN PROLACTIN RECEPTORS

This is a division of copending parent application Ser. No. 08/806,597 filed Feb. 26, 1997, in which benefit under 35 USC §119(e) of provisional application U.S. Ser. No. 60/012,503 filed Feb. 29, 1996, is claimed.

BACKGROUND OF THE INVENTION

1. Field of the Invention

The invention relates to polypeptides corresponding to soluble isoforms of human prolactin receptor and functional derivatives thereof. The invention also relates to recombinant DNA molecules encoding soluble human prolactin receptors, expression vectors carrying the recombinant DNA molecules and host cells carrying such expression vectors and capable of expressing a soluble human prolactin receptor.

2. Description of the Background Art

Two of the adenohypophysial pepside hormones, prolactin (PRL) and growth hormone (GH), are thought to have evolved from a common ancestral gene (Kelly et al., *Recent Prog. Horm. Res.* 48: 123–164, 1993). The receptors for PRL and GH (PRLR and GHR) show high homology to each other and belong to the GH/PRL/cytokine receptor superfamily. Thus, they are also thought to be cognates of a common ancestral gene (Kelly et al., 1993, supra). The signaling pathways of PRL and GH have been recently reported to involve a receptor-associated tyrosine kinase. The common structural features of the members of this superfamily are two pairs of cysteines and the tryptophan-serine (WS) motif in the extracellular domain. In the case of PRLR, there are five cysteines in the extracellular domain, and two pairs of cysteines and the WS motif have been shown to be important for ligand binding (Rozakis-Adcock et al., *J. Biol. Chem.* 266: 16472–16477, 1991; *J. Biol. Chem.* 267: 7428–7433, 1992).

The primary structure of the mature human GH receptor is a polypeptide of 620 amino acids (aa) with an extracellular hormone-binding domain of 246 aa, a single transmembrane region, and a cytoplasmic domain of 350 amino acid residues. The extracellular domain contains seven cysteine residues and five potential N-linked glycosylation sites (Kelly et al., 1953, supra). While the structure of the mature PRL receptor from rat liver was deduced from CDNA to contain 291 amino acids with an extracellular region of 210 aa having five cysteine residues and three potential N-linked glycosylation sites, a single transmembrane region of 24 aa, and a relatively short cytoplasmic domain of 57 aa (Boutin et al, *Cell* 53: 69–77, 1988 represents a first class of receptor (short form), the structure of mature human PRLR containing 598 amino acid residues represents a second class of receptor (long form) (U.S. Pat. No. 4,992,378). Like mature rat liver GHR, this long form human PRLR has an extracellular region of 210 aa and a single transmembrane region, but a long cytoplasmic region.

Interestingly, the extracellular domain of human prolactin receptor was shown to be capable of binding both human prolactin and human growth hormone with nearly equal affinity (Boutin et al., *Mol. Endocrinol.* 3: 1455–1461, 1989). Cunningham et al., *Science* 250: 1709–1712 (1990) later reported that the binding of human growth hormone to the human prolactin receptor requires the presence of a zinc atom. In contrast, the human prolactin receptor does not require zinc in order to bind hPRL and it appears that while PRL- and GH-specific determinants on the human prolactin receptor overlap in certain areas, they are not identical (Rozakis-Adcock et al., 1992, supra).

Human GHR is known to possess several isoforms, including the GH-binding protein, secreted extracellular domain of the receptor, and GHRd3, which lacks exon 3 (Leung et al., *Nature* 330: 537–543, 1987; Urbanek et al., *J. Biol. Chem.* 268: 19025–19032, 1993). Furthermore, GH binding protein (GH-BP), which is a soluble short form of the liver GH receptor was identified in the serum of mouse (Peeters et al., *Endocrinology* 101: 1164–1179, 1977), rabbit (Ymer et al., *Mol. Cell. Endocrinol.* 41: 153–161, 1985), and human (Baumann et al., *J. Clin. Endocrinol. Metab.* 62: 134–141, 1986). There is amino acid identity of the amino-terminal sequences of the receptor and the binding protein (BP) (Leung et al., 1987)

Two independent mechanisms have been proposed for the production of the GH-BP: specific proteolysis of the membrane form of the receptor or translation from an alternatively spliced mRNA, produced from the same gene as the GH receptor. In man, cow, and rabbit, the serum GH-BP probably results from proteolytic cleavage of the receptor, because only a single mRNA transcript of 4.5 Kb has been clearly identified by Northern analysis. In mouse and rat liver, two mRNAS of approximately 4.5 and 1–1.5 kilobases (kb) are expressed, which encode the membrane receptor and the GH-BP, respectively (Smith and Talamantes et al., *J. Biol. Chem.* 262: 2213–2219, 1987; Baumbach et al., *Genes Dev.* 3: 1199–1205, 1989). In rat and mouse, the GH-BP is distinguished by a short hydrophilic C-terminal extension that is not found in the membrane receptor. Using an antibody raised against a synthetic peptide containing the 17-aa hydrophilic sequence, it was clearly shown that the GH BP in rat serum is derived almost entirely from the GH BP mRNA and not from proteolytic processing of the GH receptor (Sadeghi et al., *Mol. Cell. Endocrinol.* 4: 1799–1805, 1990), probably as a result of alternative splicing of a primary transcript.

In the rat, a mutant form of the PRL receptor was identified in the Nb2 lymphoma cell line, which is dependent on PRL for growth and contains high-affinity PRL receptors (Gout et al., *Cancer Res.* 40: 2433–2436, 1980; Shiu et al., Endocrinology 113: 159–165, 1983). Biochemical studies have suggested that the receptor in these cells is different from the short and long forms already identified. Using the polymerase chain reaction of reverse-transcribed RNA and classical screening of a cDNA library, it was shown that the rat Nb2 PRL, receptor is intermediate in size (393 aa) and appears to be due to a mutation in the PRL receptor gene, resulting in a loss of 594 bp in a region encoding a major portion of the cytoplasmic domain of the long form of the PRL receptor (Ali et al., 1991, supra). However, this mutant form of the rat PRL receptor still retains the transmembrane region and a portion of the cytoplasmic domain and is not a soluble isoform of PRLR. FIG. 1 shows a schematic presentation of the GH/PRL receptor family.

In a human breast cancer cell line, a cDNA obtained from a transcript was characterized and presumed to code for a soluble extracellular domain of the hPRL receptor where the transmembrane domain exon of hPRLR is deleted and results in a frameshift mutation after $Ser^{204}$ and a stop codon after two additional residues, $Ala^{205}$ and $Trp^{206}$ (Fuh et al., *J. Biol. Chem.* 270: 13133–13137, 1995). This is the only hPRLR cDNA reported to be transcribed from an alternatively spliced form of hPRLR transcripts.

GH is known to promote water and electrolyte transport and calcium absorption in the gastrointestinal (GI) tract, (Lobie et al., 1990, supra and references cited therein). The proliferative functions of GH haste been reported as well. Administration of GH restores the intestinal and gastric mucosal weight after hypophysectomy in the rat (Scow et al., *Endocrinol.* 77: 852–858, 1965) and is protective against gastric ulceration (Winawer et al., *Arch. Intern. Med.* 135: 569–572, 1975) Also, overexpression of bovine GH enhances growth of small intestine in the transgenic mice (Ulshen et al., *Gastroenterology* 104: 973–980, 1993), and the growth of fetal rat intestinal transplants is GH dependent (Cooke et al., *Biol. Neonate* 49: 211–218, 1986). More recently, using GH-deficient rats, Lobbi et al. (Lobie et al., *Endocrinology* 130: 3015–3024, 1992) clearly demonstrated that GH stimulates proliferation and enlargement of the gastric mucosa without significant alteration in cellular composition. Furthermore, they showed that GH administration results in stimulation of gastric mucosal intrinsic factor content in parietal and chief cells in the rat. It was reported that hypophysectomy results in a decreased level of plasma gastrin and in hypotrophy of the GI tract (Enochs et al., *Gastroenterology* 70: 727, 1976) and that GH exerts the opposite effects as well as an increase of the plasma gastrin level (Enochs et al., supra; Scow et al., supra). Thus, in addition to the effect of GH and its action via insulin-like growth factor I secretion, the trophic effect of GH on the GI tract is thought to be at least partially mediated by gastrin In contrast to GH, functions of PRL in the mammalian GI tract have not been well established. PRL acts on water and electrolyte transport as well as on calcium absorption (Dusanter-Fourt et al., 1992, supra, and references cited therein). PRL in the milk is transferred into the blood circulation of neonates and may modulate the development of neuroendocrine, reproductive, and immune systems (Grosvenor et al., *Endocrine Rev.* 14: 710–728, 1992). The intestinal mucosal mass is known to increase during lactation in the rat. This trophic effect of PRL was examined using PRL-treated adult rats, and it was reported that hyperprolactinemia did not result in such changes in villus height, crypt depth, or mucosal weight, although breast hyperplasia and increase in mammary pad weight did occur (Goodlad et al., *Balliere's Clin. Gastroenterol.* 4: 97–118, 1990). However, it was also reported that inhibition of PRL secretion by bromocriptine inhibits the increase in the intestinal weight (Goodlad et al., 1990, supra); thus, hormones such as steroids or GI tract trophic hormones should be considered along with PRL for such effects.

It is now widely accepted that PRL and GH immunomodulation such as the proliferation of lymphocytes from spleens or lymph nodes of ovariectomized rats, and increase in cytotoxic activities of natural killer cells (Kelly et al., 1993, supra). Although no severe clinical disturbance in immune function has been reported for GH- or PRL-deficient patients, PRL and GH are capable of restoring immune function in hypophysectomized animal models or genetic dwarf mice (Kelly et al., 1993, supra) In vitro studies have also shows direct effects of these hormones as immunostimulatory factors on lymphocytes (Kelly et al., 1993, supra). Furthermore, expression of PRL, GH, and their receptors in lymphocytes has been well documented (Kelly et al., 1993, supra; Pellegrini et al., *Mol. Endocrinol.* 6: 1023–1031, 1992). Considering the importance of the GI tract as an immunologic barrier against foreign pathogens, there two hormones may act on immune cells in this tissue. The fact that lymphocytes, and perhaps other GH or PRL target cells are capable of producing these hormones suggests that they should be also considered "growth factors", acting via classical paracrine or autocrine pathways.

SUMMARY OF THE INVENTION

The present invention is based on the discovery that differentially spliced mRNA arc present in various human tissues, such as human gastrointestinal tissue from the upper segments of the intestine and human liver, and encode soluble isoforms of human prolactin receptor.

It is an object of the invention to provide a soluble form of human prolactin receptor which is obtainable from human intestine, or a functional derivative thereof.

One object of the invention is to provide a soluble form of human prolactin receptor which is capable of binding to human prolactin or human growth hormone and regulate the biological activity of the hormone.

A further object of the invention is to provide a recombinant DNA molecule encoding soluble human prolactin receptor.

Still another object of the invention is to provide an expression vector carrying the recombinant molecule encoding soluble human prolactin receptor.

Yet another object of the invention is to provide host cells with the recombinant DNA molecule encoding soluble human prolactin receptor and capable of expressing and producing a polypeptide of the soluble human prolactin receptor.

BRIEF DESCRIPTION OF THE DRAWINGS

FIG. 5 shows the partial flanking nucleotide and amino acid sequences (with numbering and sequences referring to sequences represented in Boutin et al., 1989, supra) surrounding the deletion sites in clones A–F, From FIG. 4 above. The nucleotide sequences of clones A, B, D, E and F, designated SEQ ID NOs: 1, 3, 5, 7 and 13 respectively, and the amino acid sequences of clones A, B, D, E and F, likewise designated SEQ ID NOs: 2, 4, 6, 8 and 14, respectively, are not shown in this figure. The partial flanking nucleotide and amino acid sequences of clone C and F, designated SEQ ID NOs: 9 and 10, and SEQ ID NOs: 11 and 12, respectively, are shown.

DETAILED DESCRIPTION OF THE INVENTION

Figure 1:
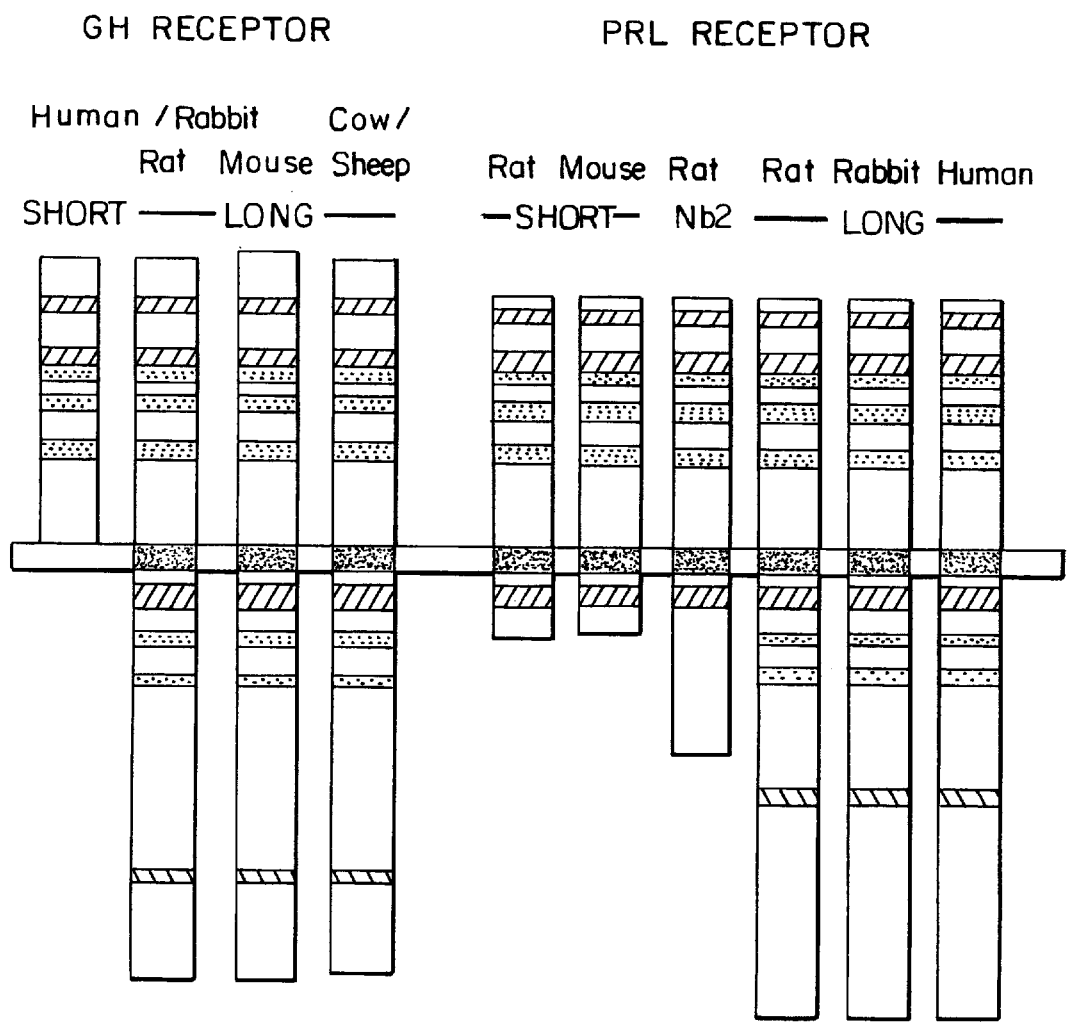
FIG. 1 is a schematic representation of the GH/PRL receptor family. The long and short (binding protein) forms of the GH receptor in human, rabbit, cow, sheep, mouse, and rat are compared to the short form of PRL receptor in rat and mouse, the intermediate Nb2 form, and the long form in rat, rabbit, cow, and human. The transmembrane domains are shown in black. Regions of increased (>68%) amino acid identity are cross-hatched and those of moderate (40–60%) identity are stippled.

The present invention is based on the unexpected discovery that differentially spliced mRNA transcripts encoding at least one soluble isoform of human prolactin were present in various human tissues and cell lines. These differentially spliced mRNA transcripts are smaller in size than the expected full length human PRLR transcript, and when reversed transcribed into cDNA and amplified, several of these transcripts were found to encode soluble isoforms of human PRLR which all lack the transmembrane and cytoplasmic domains.

In the context of the present invention the terms "soluble human prolactin receptor" or "soluble isoforms of human prolactin receptor" are intended to encompass any isolated, purified soluble human prolactin receptor from natural sources, such as human serum, or derived from expression systems for recombinant human prolactin receptor, or chemically synthesized. The term is also intended to include polypeptides or proteins substantially corresponding to soluble isoforms of human prolactin receptor having human prolactin-binding and/or human growth hormone-binding activity. Also included within the scope of this term are salts and functional derivatives of any such polypeptides or protein.

A polypeptide or protein "substantially corresponding" to soluble human prolactin receptors (hPRLR) includes not only soluble hPRLR but also polypeptides or proteins that are "muteins" of soluble hPRLR.

"Muteins" that substantially correspond to soluble hPRLR are those polypeptides in which one or more amino acid of the soluble hPRLR amino acid sequence have been replaced with another amino acid and/or deleted, provided that the resulting protein exhibits substantially the same or higher biological activity as the soluble hPRLR. The "biological activity" of the soluble hPRLR as used herein as specifically meant to include the binding activity (e.g., human prolactin-binding, human growth hormone-binding) or inhibiting activity thereof (e.g. to human prolactin and/or human growth hormone).

In order to substantially correspond to the soluble isoforms of human prolactin receptor, the changes in the sequence are generally relatively minor. Although the number of changes may be more than ten, preferably there are no more than ten changes, more preferably no more than five, and most preferably no more than three such changes. While any technique can be used to find potentially biologically active proteins which substantially correspond to soluble hPRLR, one such technique is the use of conventional mutagenesis techniques on the DNA encoding the protein, resulting in a few modifications. The proteins expressed by such clones can then be screened for binding or hormone-inhibitory activity.

"Conservative" changes are those changes which would not be expected to change the activity of the protein and are usually the first to be screened as these would not be expected to substantially change the size, charge or configuration of the protein and thus would not be expected to change the biological properties thereof.

Conservative substitutions of soluble hPRLR include a mutein wherein at least one amino acid residue in the polypeptide has been conservatively replaced by a different amino acid. Such substitutions preferably are made in accordance with the following list as presented in Table IA, which substitutions may be determined by routine experimentation to provide modified structural and functional properties of a synthesized polypeptide molecule while maintaining the biological activity characteristic of soluble hPRLR.

TABLE IA

| Original Residue | Exemplary Substitution |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

Alternatively, another group of substitutions of soluble hPRLR are those in which at least one amino acid residue in the polypeptide has been removed and a different residue inserted in its place according to the following Table IB. The types of substitutions which may be made in the polypeptide may be based on analysis of the frequencies of amino acid changes between a homologous protein of different species, such as those presented in Table 1-2 of Schulz et al., G.E., Principles of Protein Structure Springer-Verlag, New York, N.Y., 1798, and FIGS. 3–9 of Creighton, T. E., Proteins: Structure and Molecular Properties, W.H. Freeman & Co., San Francisco, Calif. 1983. Based on such an analysis, alternative conservative substitutions are defined herein as exchanges within one of the following five groups:

TABLE IB

1. Small aliphatic, nonpolar or slightly polar residues: Ala, Ser, Thr (Pro, Gly);
2. Polar negatively charged residues and their amides: Asp, Asn, Glu, Gln;
3. Polar, positively charged residues: His, Arg, Lys;

TABLE IB-continued

4. Large aliphatic nonpolar residues:
   Met, Leu, Ile, Val (Cys); and
5. Large aromatic residues: Phe; Tyr, Trp.

The three amino acid residues in parentheses above have special roles in protein architecture. Gly is the only residue lacking any side chain and thus imparts flexibility to the chain. This however tends to promote the formation of secondary structure other than α-helical. Pro, because of its tends to promote β-turn-like structures, although in some cases Cys can be capable of participating in disulfide bond formation which is important in protein folding. Note that Schulz et al., supra, would merge Groups 1 and 2, above. Note also that Tyr, because of its hydrogen bonding potential, has significant kinship with Ser, and Thr, etc.

Conservative amino acid substitutions according to the present invention, e.g., as presented above, are known in the art and would be expected to maintain biological and structural properties of the polypeptide after amino acid substitution. Most deletions and substitutions according to the present invention are those which do not produce radical changes in the characteristics of the protein or polypeptide molecule. "Characteristics" is defined in a non-inclusive manner to define both changes in secondary structure, e.g. α-helix or β-sheet, as well as changes in biological activity, e.g. binding or inhibition of human PRL or human GH.

Examples of production of amino acid substitutions in proteins which can be used for obtaining muteins of soluble hPRLR for use in the present invention include any known method steps, such as presented in U.S. Pat. RE Nos. 33,653, 4,959,314, 4,588,585 and 4,737,462, to Mark et al.; 5,116,943 to Koths et al., 4,965,195 to Namen et al.; 4,879,111 to Chong et al.; and 5,017,691 to Lee et al.; and lysine substituted proteins presented in U.S. Pat. No. 4,904,584 (Shaw et al.).

One way to determine which portions of the molecule would be most likely to permit such changes without affecting the binding or inhibitory activity is to first test the effect of changes in the soluble hPRLR. It has been shown in Rozakis-Adcock et al., 1991, supra, that changes to any of the first four cysteine residues in human PRLR affected receptor binding activity. Likewise, the WS motif appears to be an important structural element in regulating ligand binding and selective mutations of these residues resulted in a reduction in affinity for PRL, (Rozakis-Adcock et al., 1992, supra). A discussion of identifying ligand-binding determinants is discussed in Kelly et al., 1993, supra, herein incorporated by reference.

Besides conservative substitutions discussed above which would not significantly chancre the activity of soluble hPRLR, either conservative substitutions or less conservative and more random changes, which lead to an increase in biological activity of soluble, are intended to be within the scope of the invention.

When the exact effect of the substitution or deletion is to be confirmed, one skilled in the art will appreciate that the effect of the substitution(s), deletion(s), etc. will be evaluated by routine ligand binding assays. Screening using such a standard test does not involve undue experimentation.

At the genetic level, these muteins are generally prepared by site-directed mutagenesis of nucleotides in the DNA encoding the soluble hPRLR, thereby producing DNA encoding the mutein, and thereafter synthesizing the DNA and expressing the polypeptide in recombinant cell culture. The muteins typically exhibit the same or increased qualitative biological activity as the naturally occurring protein, Ausubel et al., Current Protocols in *Molecular Biology*, Greene Publications and Wiley Interscience, New York, N.Y., 1987–1995; Sambrook et al., Molecular Cloning: A Laboratory Manual, Cold Spring Harbor Laboratory, Cold Spring Harbor, N.Y., 1989.

Preparation of a soluble hPRLR mutein in accordance herewith, or an alternative nucleotide sequence encoding the same polypeptide but differing from the natural sequence due to changes permitted by the known degeneracy of the genetic code, can be achieved by site-specific mutagenesis of DNA that encodes an earlier prepared mutein or a nonmutein version of the soluble hPRLR. Site-specific mutagenesis allows the production of muteins through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 25 complementing nucleotides on each side of the sequence being altered. In general, the technique of site-specific mutagenesis is well known in the art, as exemplified by publications such as Adelman et al., *DNA* 2:183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981), the disclosure of which is incorporated herein by reference. These phage are readily available commercially and their use is generally well known to those skilled in the art. Alternatively, plasmid vectors that contain a single-stranded phage origin of replication (Veira et al., *Meth. Enzymol.* 153:3, 1987) may be employed to obtain single-stranded DNA.

In general, site-directed mutagenesis in accordance herewith is performed by first obtaining a single-stranded vector that includes within its sequence a DNA sequence that encodes the relevant polypeptide. An oligonucleotide primer bearing the desired mutated sequence is prepared synthetically by automated DNA/oligonucleotide synthesis. This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells, such as *E. coli* JM101 cells, and clones are selected that include recombinant vectors bearing the mutated sequence arrangement.

After such a clone is selected, the mutated soluble hPRLR may be removed and placed in an appropriate vector, generally a transfer or expression vector of the type that may be employed for transfection of an appropriate host.

Accordingly, gene or nucleic acid encoding for a soluble hPRLR can also be detected, obtained and/or modified, in vitro, in situ and/or in vivo, by the use of known DNA or RNA amplification techniques, such as PCR and chemical oligonucleotide synthesis. PCR allows for the amplification (increase in number) of specific DNA sequences by repeated DNA polymerase reactions. This reaction can be used as a replacement for cloning; all that is required is a knowledge of the nucleic acid sequence. In order to carry out PCR, primers are designed which are complementary to the sequence of interest. The primers are then generated by automated DNA synthesis. Because primers can be designed to hybridize to any part of the gene, conditions can be created such that mismatches in complementary base pairing can be tolerated. Amplification of these mismatched regions can lead to the synthesis of a mutagenized product resulting in the generation of a peptide with new properties (i.e., site directed mutagenesis). See also, e.g., Ausubel, supra, Ch. 16. Also, by coupling complementary DNA (cDNA) synthesis, using reverse transcriptase, with PCR, RNA can be used as the starting material for the synthesis of the extracellular domain of a prolactin receptor without cloning.

Furthermore, PCR primers can be designed to incorporate new restriction sites or other features such as termination codons at the ends of the gene segment to be amplified. This placement of restriction sites at the 5' and 3'ends of the amplified gene sequence allows for gene segments encoding soluble hPRLR or a fragment thereof to be custom designed for ligation with signal sequences and/or cloning sites in vectors.

PCR and other methods of amplification of RNA and/or DNA are well known in the art and can be used according to the present invention without undue experimentation, based on the teaching and guidance presented herein. Known methods of DNA or RNA amplification include, but are not limited to polymerase chain reaction (PCR) and related amplification processes (see, e.g. , U.S. Pat. Nos. 4,683,195, 4,683,202, 4,800,159, 4,965,288, to Mullis et al. 4,795,699 and 4,921,794 to Tabor et al.; 5,142,033 to Innis; 5,122,464 to Wilson et al.; 5,091,310 to Innis; 5,066,584 to Gyllensten, et al.; 4,889,818 to Gelfand et al.; 4,994,370 to Silver et al.; 4,766,067 to Biswas; 4,656,134 to Ringold; and Innis et al., eds., *PCR Protocols: A Guide to Method and Applications*) and RNA mediated amplification which uses anti-sense RNA to the target sequence as a template for double stranded DNA synthesis (U.S. Pat. No. 5,130,238 to Malek et al., with the tradename NASBA); and immuno-PCR which combines the use of DNA amplification with antibody labeling (Ruzicka et al., *Science* 260:487 (1993); Sano et al., *Science* 258:120 (1992); Sano et al., *Biotechniques* 9:1378 (1991)), the entire contents of which patents and reference are entirely incorporated herein by reference.

As used herein, the term "salts" refers to both salts of carboxyl groups and to acid addition salts of amino groups of the polypeptide molecule. Salts of a carboxyl group may be formed by means known in the art and include inorganic salts, for example, sodium, calcium, ammonium, ferric or zinc salts, and the like, and salts with organic bases as those formed, for example, with amine, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic aid or oxalic acid.

"Derivatives" as used herein covers derivatives which may be prepared from the functional groups which occur as side chains on the residues or the N- or C-terminal groups by means known in the art, and are included in the invention. Derivatives may have chemical moieties such as carbohydrate or phosphate residues, provided such a fraction has the same or higher biological activity as soluble hPRLR.

For example, derivatives may include aliphatic esters of the carboxyl groups, amides of the carboxyl groups by reaction with ammonia or with primary or secondary amines, N-acyl derivatives or free amino groups of the amino acid residues formed with acyl moieties (e.g., alkanoyl or carbocyclic aroyl groups) or O-acyl derivatives of free hydroxyl group (for example that of seryl or threonyl residues) formed with acyl moieties.

The term "derivatives" is intended to include only those derivatives that do not change one amino acid to another of the twenty commonly occurring natural amino acids.

Although soluble hPRLR is a protein or polypeptide, it is a sequence of amino acid residues. A polypeptide consisting of a larger sequence which includes the entire sequence of a soluble hPRLR polypeptide, in accordance with the definitions herein, is intended to be included within the scope of a polypeptide "consisting essentially of" soluble hPRLR as long as the additions do not affect the basic and novel characteristics of the invention, i.e., if they either retain or increase the biological activity of soluble hPRLR or can be cleaved to leave a protein or polypeptide having the biological activity of soluble hRPLR. Similarly, a protein or polypeptide "comprising" soluble hRLR is intended to include a protein or polypeptide of any length which includes the entire sequence of soluble hPRLR polypeptide as defined herein. Thus, for example, the present invention is intended to include fusion proteins of soluble hPRLR with other amino acids or peptides.

A recombinant DNA molecule encoding a soluble hPRLR of the present invention can be obtained by cDNA cloning, and in a preferred embodiment, the cDNA will be incorporated into a replicable expression vector such as a plasmid capable of autonomous replication in recipient host cells.

By "cDNA" is meant complementary DNA produced from an RNA template by the action of RNA-dependent DNA polymerase (reverse transcriptase). Thus a "cDNA clones" means a duplex DNA sequence complementary to an RNA molecule of interest.

Standard reference works setting forth the general principles of recombinant DNA technology include Ausubel et al., eds., *Current Protocols In Molecular Biology*, Green Publishing Assoc. and Wiley Interscience, N.Y. (1987–1995), Watson et al., *Molecular Biology of the Gene*, Volumes I and II, The Benjamin/Cummings Publishing Company, Inc., publisher, Menlo Park, Calif. (1987); Darnell et al., *Molecular Cell Biology*, Scientific American Books, Inc., publisher, New York, N.Y. (1986); Lewin, *Genes II*, John Wiley & Sons, publishers, New York, N.Y. (1985); Old et al., *Principles of Gene Manipulation*: An Introduction to Genetic Engineering, 2d edition, University of California Press, publisher, Berkeley, Calif. (1981); and Sambrook et al., *Molecular Cloning: A Laboratory Manual*, Cold Spring Harbor Laboratory, Cold Spring Harbor, N.Y. (1989). These references are hereby incorporated by reference.

In order to be capable of expressing the soluble hPRLR, an expression vector should have specific nucleotide sequences containing transcriptional and translational regulatory information linked to the DNA coding for the soluble hPRLR in such a way as to permit gene expression and production of the protein. First, in order for the gene to be transcribed, it must be preceded by a promoter recognizable by RNA polymerase, to which the polymerase binds and thus initiates the transcription process.

A nucleic acid molecule, such as DNA, is said to be "capable of expressing" a polypeptide, such as soluble hPRLR, if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The regulatory regions needed for gene expression in general include a promoter region as well as the DNA sequences which, when transcribed into RNA, will signal the initiation of protein synthesis. Such regions will normally include those 5'-noncoding sequences involved with initiation of transcription and translation.

Two DNA sequences (such as a promoter region sequence and a coding sequence) are said to be operably linked if the nature of the linkage between the two DNA sequences does not (1) result in the introduction of a frame-shift mutation, (2) interfere with the ability of the promoter region sequence to direct the transcription of the coding sequence, or (3) interfere with the ability of the coding sequence to be transcribed by the promoter region sequence. A promoter region would be operably linked to a DNA sequence if the promoter were capable of effecting, transcription of that DNA sequence. Thus, to express the protein, transcriptional and translational signals recognized by the host cell are necessary.

A promoter is a double-stranded DNA or RNA molecule which is capable of binding RNA polymerase and promoting the transcription of an "operably linked" nucleic acid sequence. As used herein, a "promoter sequence" is the sequence of the promoter which is found on the DNA or RNA and is transcribed by the RNA polymerase.

There are a variety of promoters in use, which work with different efficiencies (strong and weak promoters) that can be employed with a variety of translational regulatory signals, depending upon the nature of the host. They may be derived from viral sources, such as adenovirus, cytomegalovirus (CMV), bovine papilloma virus, Simian virus, or the like, where the regulatory signals are associated with a particular gene having a high level of expression. Examples are the TK promoter of Herpes virus, the SV40 early promoter, the yeast ga14 gene promoter, baculovirus late or very late promoters such as the polyhedrin promoter, etc. Alternatively, promoters from mammalian expression products, such as actin, collagen, myosin, etc. may be employed.

The DNA molecule comprising the nucleotide sequence coding for soluble hPRLR of the invention, and the operably linked transcriptional and translational regulatory signals can be inserted into a vector which is capable of integrating the desired gene sequences into the host cell chromosome. In order to be able to select the cells which have stably integrated the introduced DNA into their chromosomes, one or more markers which allow for selection of host cells which contain the expression vector is used. The marker may provide for prototropy to an auxotrophic host, biocide resistance, e.g., antibiotics, or heavy metals, such as copper, or the like. The selectable marker gene can either be directly linked to the DNA gene sequences to be expressed, or introduced into the same cell by cotransfection. Additional elements may also be needed for optimal synthesis of mRNA. These elements may include splice signals, as well as transcription promoters, enhancers, and termination signals. cDNA expression vectors incorporating such elements include those described by Okayama, *Mol. Cel. Biol.* 3:280, 1983.

In a preferred embodiment, the introduced DNA molecule will be incorporated into a plasmid or viral vector capable of autonomous replication in the recipient host. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred eukaryotic plasmids include BPV, vaccinia, SV40, 2-micron circle, etc., or their derivatives, such as pECE, pKCR2, pcDNA3 or pRc/CMV (Invitrogen, San Diego, Calif.) and the like. Such plasmids are well known in the art (Botstein et al., *Miami Winter Symp.* 19:265–274, 1982; Broach, in *The Molecular Biology of the Yeast Saccharomyces: Life Cycle and Inheritance*, Cold Spring Harbor Laboratory, Cold Spring Harbor, N.Y., pp. 445–470, 1981; Broach, *Cell* 28:203–204, 1982; Bollon et al., *J. Clin. Hematol. Oncol.* 10:39–48, 1980; Maniatis, in *Cell Biology: A Comprehensive Treatise*, Vol. 3: *Gene Expression*, Academic Press, New York, pp 563–608, 1980).

Once the vector or DNA sequence containing the construct(s) has been prepared for expression, the expression vector may be introduced into an appropriate host cell by any variety of suitable means, such as transformation, transfection, lipofection, conjugation, protoplast fusion, electroporation, calcium phosphate precipitation, direct microinjection, etc.

Eukaryotic host cells can be mammalian cells, e.g., human, monkey (COS cells), mouse and chinese hamster ovary (CHO) cells, because they provide post-translational modifications to protein molecules including correct folding, correct disulfide bond formation as well as glycosylation at correct sites. However, yeast cells and insect cells, e.g. baculovirus, can overproduce soluble receptor polypeptide and can also carry out post-translational peptide modifications including glycosylation. As an example of introducing an expression vector into a host, chinese hamster ovary (CHO) or monkey kidney cells (COS-7) can be grown to about 50% confluence and treated with calcium phosphate to permeate cells. These cells can then be transferred with 10 μg of vector DNA such pECE-soluble hPRLR cDNA and stable transfectants can be isolated for production of soluble hPRLR.

In order for the soluble hPRLRs of the invention to be secreted as soluble isoforms, the DNA sequence encoding the soluble hourly must also be directly joined to a DNA sequence encoding a signal peptide. This linkage allows for translation of a polypeptide that is transitionally in frame with the signal peptide and capable of being secreted from the host cell. While it is preferable that the signal peptide be provided by the cloned cDNA itself, it is possible that another signal peptide can be used to facilitate secretion of soluble hPRLR.

The soluble hPRLRs according to the present invention can be used to bind human prolactin and/or human growth hormone as a binding protein. Accordingly, soluble hPRLRs functioning as a human prolactin and/or human growth hormone binding protein can be used either in diagnostics for the detection and measurement of the binding ligand or in therapeutics for binding to human prolactin and/or human growth hormone in order to retard or inhibit their hormone activities.

With regard to diagnostics, soluble receptors can also be used in place of monoclonal antibodies to provide solution-based radioligand receptor assays. Similarly, antibody-receptor sandwich assays or enzymatic assays can be performed with the soluble hPRLR of the present invention.

Furthermore, essentially pure soluble hPRLR can also be used in x-ray crystallographic analysis to develop molecular models which define the tertiary structure of the hormone-binding domains. Such information would provide insight into the structure of the actual contact between a hormone and its receptor. Structural information of this sort would be useful in the design of peptides which have prolactin or growth hormone-like agonistic or antagonistic activity.

Having now generally described the invention, the same will be more readily understood through reference to the following example which is provided by way of illustration and is not intended to be limiting of the present invention.

EXAMPLE 1

To better understand the physiological functions of PRL and GH on the GI tract, the tissue and cellular distribution of their receptor transcripts were characterized in 1) epithelial cells isolated from the stomach, small intestine, and colon in the human, rabbit, and rat, and also in mouse intraepithelial lymphocytes; 2) enriched preparations of rabbit gastric parietal, chief, and mucus-secreting cells; and 3) human gastric and colorectal tumors, whether or not they were associated with liver metastasis. Biological effects of GH and PRL in the GI tract were investigated on mucin and acid secretion in vitro, using a human colonic cancer cell line and freshly isolated rabbit gastric cells. Several human PRLR isoforms were also characterized in the normal tissue, tumor biopsies, and gastrointestinal and breast cancer cell lines.

Materials and Methods

Cell culture. The human colonic cells Caco-2 and HT-29 were obtained from Dr. J. Fogh (Sloan Kettering Institute for Cancer Research, Rye, N.Y.). Caco-2 cells exhibit an enterocytelike phenotype during the exponential phase of growth and are fully differentiated enterocytes 10–15 days after the acquisition of confluency. The mucus-secreting cell lines RT-29-MTX and HT-29-S-B6 were selected from the parental HT-29 cells after adaptation to methotrexate ($10^{-6}$M) and serum privation, respectively (Forgue-Lafitte et al., *Cancer Res.* 52: 6827–6831; Lesuffler et al., *Cancer Res.* 50: 6334–6343, 1990). Similarly, mucus-secreting HT-29-5-FU cells were isolated after progressive adaptation to 5-fluorouracil (Lesuffleur et al., *Int. J. Cancer* 49: 731–737, 1992). HT-29-5-FU cells are composed of 80% polarized undifferentiated cells and 20% mucin-secreting cells. The human gastric cancer cell lines HGT-1, MKN-28, and MKN-74 were respectively established from a primary tumor localized in the fundus (Laboisse et al., *Cancer Res.* 42: 1541–1548, 1982) or well-differentiated adenocarcinomas (Hojo et al., *Miigata Igakukai Zassi* 91: 737–763). The human breast cancer cell line, T-47D, was cultured as reported previously (Boutin et al., *Mol. Endocrinol.* 3: 1455–1461, 1989). All cell lines, except for the HT-29-S-B6 subclone, were grown in Dulbecco's modified Eagle's medium (DMEM) supplemented with 8 mnmol/l of L-glutamine, antibiotics, and 5–20% fetal calf serum, in an atmosphere of 95% air-5% $CO_2$ at 37° C. HT-29-S-E6 cells were maintained in serum-free DMEM:Ham's F-12 (1:1) medium. Cells were passaged weekly in a 1:10 split ratio, with the use of 0.01% (wt/vol) trypsin-0.04% (wt/vol) EDTA. For biological assays, HT-29-MTX cells were grown in DMEM supplemented with 10% fetal calf serum containing penicillin (100 U/ml) and streptomycin (100 m,g/ml). When these cells were grown on 24-mm polycarbonate transwell culture dishes (Costar), they were seeded at $2 \times 10^6$ cells/well.

Preparation of gastric and intestinal tissues. Human surgical specimens from patients who underwent gastrectomy, duodeno-pancreatectomy, or colectomy were obtained from the Centre de Chirurgie Digestive (Pr. Parc, Hopital Saint-Antoine, Paris, France). Human colorectal tumors were graded according to the Dukes' classification, modified by Astler and Coller (Aster et al., *Ann. Surg.* 139: 846–851, 1954). Pathological and normal tissues were dissected, snap frozen in liquid nitrogen, and stored at −80° C. until RNA extraction.

For preparation of human and rat epithelial cells, fresh samples of intestine or stomach were washed in ice-cold Krebs-Ringer phosphate buffer containing (in mM) 118 NaCl, 5 KCl, 1.2 $MgSO_4$, 1.2 $KH_2PO_4$, and 10 $Na_2HPO_4$ (pH 7.5) and soaked in a solution containing 2.5 mM EDTA (pH 7.5) and 250 mM NaCl for 30 min at 4° C. Epithelial cells were obtained by serial shaking of the samples in the same solution, as previously described (Chastre et al., *Endocrinology* 121: 2211–2221, 1987).

The enriched preparation of rabbit gastric parietal, chief, and mucous cells was carried out following the collagenase/EDTA procedure (Choquet et al., *J. Pharmacol. Exp. Ther.* 266: 1306–1311). Cell separation was performed by counterflow centrifugation using a Beckman elutriator rotor JE6-B. Three elutriation fractions were collected at a rotor speed of 2,100 revolutions per minute by increasing the flow rate from 24 to 43 and 67 ml/min. The first fraction (F1 cells) mainly contained 80% mucous cells and was devoid of parietal or chief cells, the second fraction (F2 cells) contained about −40–45% of pepsin-secreting chief cells, and the third fraction (F3 cells) contained 65–70% of acid-secreting parietal cells. Experiments were also conducted on highly purified parietal cells. Fractions F2 and F3 were layered onto Nycodenz gradient (density 1.04–1.08), according to the method previously reported (Choquet et al., 1993, supra, and references therein). This purified cell fraction contained 90–95% pure parietal cells.

Mouse intraepithelial lymphocytes were prepared from small intestinal mucosa, as previously described (Guy-Grand et al., *J. Exp. Med.* 148: 1661–1677, 1978).

Reverse transcription-polymerase chain reaction (RT-PCR). Total RNA was isolated by guanidinium isothiocyanate extraction and cesium chloride density gradient ultracentrifugation. Five micrograms of total RNA were reverse transcribed under the following conditions: (in mM) 20 tris(hydroxymethyl)aminomethane (Tris)-HCl (pH 8.3), 50 KCl, 5 $MgC_2$, 10 dithiothreitol, 1 each of deoxynucleotide triphosphates, 1 μg of random primer (Boehringer Mannheim, Indianapolis, Ind.), 1 μg of oligo(dT) primer (Pharmacia, Piscataway, N.J.), 30 U of RNasin (Promega, Madison, Wis.), and 200 U of Molony murine leukemia virus reverse transcriptase (GIBCO BRL, Gaithersburg, Md.) In 30 μl of final volume. The reaction mixtures were incubated at 37° C. for 1 h. The RT reactions were terminated by heating at 96° C. for 5 min and quick-chilled on ice. Six microliters of RT reaction (equivalent to 1 μm of total RNA) were transferred to a PCR mixture (50 μl of final volume) containing (in mM) 20 Tris-HCl (pH 8.3), 50 KCl, 2.0 $MgCl_2$, 1 U of Taq polymerase (Perkin-Elmer Cetus), and forward and reverse primers.

Amplifications were carried out in an automatic thermal cycler (GeneAmp PCR system 9600, Perkin-Elmer Cetus). The primers and corresponding amplification profiles used for each target transcript were as follows: 1) human PRLR:HPR-17SHPR-12S, 30 sec at 94° C., 1 min 30 sec at 65° C., 1 min 30 sec at 72° C., 30 cycles; RPR-4S/HPR-28, 30 sec at 94° C., 1 min at 65° C., 1 min at 72° C., 35 cycles. 2) Rat PRLR: RPP-F1/RPR-R1, 30 sec at 94° C., 1 min 30 sec at 65° C., 1 min at 72° C., 30 cycles; RPR-F1/RPR-R2, 30 sec at 94° C., 1 min 30 sec at 65° C., 1 min at 72° C., 30 cycles; RPR-7S/RPR-2S, 30 sec at 94° C., 1 min 30 sec at 65° C., 1 min at 72° C., 30 cycles. 3) Rabbit PRLR: RPR4S/CL3, 30 sec at 94° C., 1 min 30 sec at 48° C., 1 min at 72° C., 30 cycles. 4) Mouse PRLR: mPR1/mPR2, 30 sec at 94° C., 1 min 30 sec at 65° C., 1 min at 72° C., 30 cycles. 5) Mouse PRL:Ma/Md, 30 sec at 94° C., 1 min 30 sec at 65° C., 1 min at 72° C., 35 cycles. 6) Human GHR: HG0/HG15, carried out overnight with $5 \times 10^5$ counts per minute (cpm) of a probe per milliliter of a hybridization solution composed of 5×SSC (20×SSC is 3M NaCl, 0.3 M sodium citrate; pH 7.0), 0.02 M $Na_2H_2PO_4$ (pH 7.0), 7% sodium dodecyl sulfate (SDS), and 100 ng/ml salmon sperm DNA. Membranes were washed twice for 15 min with 6×SSC and 0.1% SDS. The positions of the internal oligonucleotides used as probes are indicated in Table 2, together with hybridization and washing temperatures. A film was exposed with an intensifying screen at −80° C.

TABLE 2

List of the oligonucleotides used in PCR and Southern analyses

| Target | PCR Primer Position | Southern Probe Position | Hybrid/Wash Temp | Reference No. |
|---|---|---|---|---|
| hPRLR | HPR-17S: 10–37 | | | |
| | HPR-12S: 629–656 | HPR11: 506–525 | 48° C. | Boutin et al., 1989 |
| | RPR-4S: 757–780 | | | Boutin et al., 1989 |
| | HPR-28: 1779–1805 | | | |
| hGHR | HG O: 47–66 | GHR3: 354–374 | 55° C. | Leung et al., 1987 |
| | HG 15: 427–446 | HG16: 107–126 | | Leung et al., 1987 |
| rPRLR | RPR-F1: 624–653 | | | |
| | RPR-R1: 924–953 (short) | RPR14: 786–804 | 50° C. | Boutin et al., 1988 |
| | RPR-R2: 1014–1043 (long) | | | |
| | RPR-7S: 251–276 | RPR3: 299–320 | 50° C. | Shirota et al., Mol. Endocrin. 4: |
| | RPR-2S: 508–532 | | | 1136–1143, 1990. |
| rGHR | rGHR-EV: 690–709 | GHR1: 998–1018 | 42° C. | Mathews et al., J. Biol. Chem. |
| | | | | 264: 9905–9910, 1989. |
| | rGHR-Bg: 1121–1139 | | | |
| rabPRL | RPR-45: 757–780 | RPR14: 805–819 | 50° C. | Edery et al., Proc. Natl. Acad. |
| | | | | Sci. 86: 2112–2116, 1989. |
| | CL3: 1119–1135 | | | |
| rabGHR | GHR2: 183–202 | GHR1: 805–825 | 42° C. | Leung et al., 1987 |
| | GHR5: 904–923 | | | |
| mPRLR | mPR1: 509–533 | WS2: 845–868 | 50° C. | Davis et al., Mol. Endocrinol. 3: |
| | | | | 674–680, 1989. |
| | mPR2: 932–955 | | | |
| mPRL | mA: 146–168 | mB: 320–343 | 50° C. | Linzer et al. 1985. |
| | mD: 706–730 | | | |

30 sec at 94° C., 1 min 30 sec at 65° C., 1 min at 72° C., 35 cycles. 7) Rat GHR: rGMR-EV/rGHR-Bg, 30 sec at 94° C., 1 min at 45° C., 1 min at 72° C., 35 cycles. 8) Rabbit GHR: GHR2/GHR5, 30 sec at 94° C., 1 min 30 sec at 48° C., 1 min at 72° C., 35 cycles.

Figure 2:
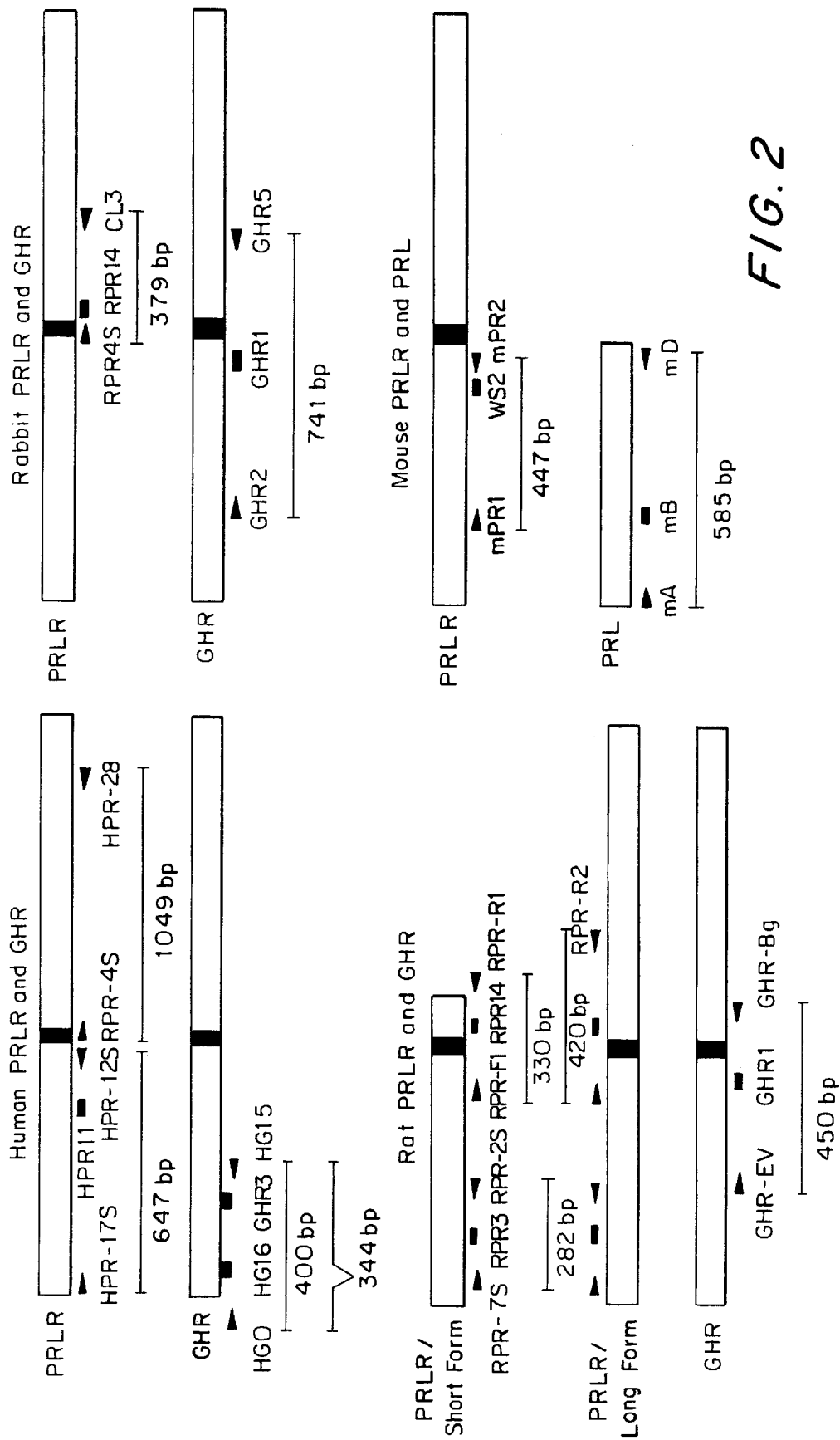
FIG. 2 is a schematic presentation of the strategy of polymerase chain reaction (PCR) and Southern analysis of prolactin (PRL) and growth hormone (GH) receptor (PRLR and GHR) expression in gastrointestinal tract. Arrowheads show PCR primers for each target gene; thick bars show probes for Southern analysis; and solid black boxed regions indicate transmembrane domain. The size of each PCR amplicon is also shown.

The positions of the primers are listed in Table 2 and FIG. 2. PCR mixtures were initially heated to 95° C. for 1 min 30 sec. Amplification was completed by an incubation at 72° C. for 10 min. Cyclophilin gene transcript was amplified as described (Pellegrini et al., 1992, supra) to verify the integrity of RNA preparations. Samples that showed clear PCR product of cyclophilin were considered useful.

A portion (10 µl) of each PCR sample was loaded on a 1.5% agarose gel, stained with ethidium bromide, and used for Southern analysis.

A negative control without RNA in the RT reaction was prepared for each experiment. All data were considered valuable only when no signal was seen for negative control after ethidium bromide staining of an agarose gel and in Southern analysis.

Southern analysis. PCR products were transferred to a positively charged nylon membrane (Zeta-Probe GT membrane, Bio-Had, Hercules, Calif.). Internal probes listed in Table 1 were end-labeled with $^{32}P$ and purified with the use of a Sephadex G-50 spin column. Hybridization was Subcloning and sequencing of PCR fragments. To subclone human PRLR isoforms, PCR samples were loaded on a 1.5% low melting point agarose gel (LMP). Appropriate bands were finely excised and heated at 65° C. for 5–10 min, and 5 µl of LMP containing PCR products were used for ligation reaction. All subclonings were carried out with the use of a TA cloning kit (Invitrogen, San Diego, Calif.) according to the procedure suggested by the manufacturer. Sequencing was performed using Sequenase version 2.0 DNA sequencing kit (United States Biochemical, Cleveland, Ohio).

Biological assays for PRL, and GH on mucin and gastric acid secretion. The effects of ovine PRL (NIDDK PRL-15, obtained from the National Hormone and Pituitary Program/National Institute of Diabetes and Digestive and Kidney Diseases, Baltimore, Md.) and recombinant human growth hormone (Saizen, Serono Laboratories, Geneva, Switzerland) were tested on the secretion of gastric M1 mucin antigen by confluent HT-29-MTX cells. Cells were placed in standard culture conditions or cultured on 24-mm polycarbonate filters (0.4 µm, Costar Transwell). PRL, GH (1–316 ng/ml), or carbamylcholine ($10^{-4}$ M) were added for 30, 60, or 180 min to the apical cell surface or to the basal adherent side of the intestinal cells in culture. Controls without effectors were run at the same time. Similar experiments were performed using the F1 fraction, containing 80% rabbit gastric mucous cells ($4 \times 10^6$ cells per flask). Isolated cells were incubate for 30–60 min under a 95% $O_2$–5%

CO$_2$ atmosphere, in the presence of either PRL, (0.01–1 µg/ml) or carbamylcholine (10$^{-4}$ M). An immunoradiometric assay of the gastric M1 mucin antigens was performed as already described with the use of a solid-phase immunosorbent assay (Bara et al., Biochem. J. 254: 185–193, 1988). Briefly, the first layer contained an anti-M1 monoclonal antibody (mAb; 1–13 M1), and the second layer was the supernatant of HT-29-MTX culture cells. The third layer was the $^{125}$I-labeled immunoglobulin G fraction from a mixture of seven different anti-M1 Mabs. As a standard, lyophilized mucinous ovarian cyst fluid containing a great amount of mucin M1 antigens was used. It was diluted in phosphate-buffered saline-Tween 20 at 10 µg/ml dry weight. For comparison purposes, it was estimated that it contained 10,000 AU of gastric M1 mucin antigens. A mixture of antiproteases (2 µg/ml aprotinin, 20 µg/ml benzamidine, 25 µM leupeptin, 25 µM antipapain, 50 µM chymostatin, 1 mM pepstatin, 5 µM bestatin, and 1 mM phenylmethylsulfonyl fluoride) was added just before the culture supernatants, which were kept at −20° C., were removed.

Acid secretion from the rabbit parietal cell fraction F3 was determined using the [$^{14}$C]-aminopyrine (AP) accumulation method as previously described (Choquet et al., 1993, supra). Cells (1.5×10$^6$ cells/ml) were incubated under a 95% O$_2$–5% CO$_2$ atmosphere at 37° C. for 20 min in standard medium containing 0.05 µCi [$^{14}$C]-AP in the presence of effectors (10$^{-4}$ carbamylcholine, 10$^{-5}$ M histamine) alone or combined with various concentrations of PRL ranging from 10$^{-11}$ to 10$^{-8}$ M. To stop the reaction, 0.4 ml of the incubation mixture were layered over 0.9 ml of ice-cold standard medium and briefly centrifuged. The pellets were suspended in 0.1 ml of 10% HClO$_4$ and the radioactivity was measured in a liquid scintillation counter. Data are obtained from five separate experiments performed in duplicate or triplicate.

Results

Distribution of PRLR and GHR gene transcripts in the gastro-intestinal tract and cell lines. FIG. 2 is a schematic presentation of the primer strategy used in PCR and Southern analysis for PRLR, GHR, and PRL transcripts. Total RNA prepared from each sample was reverse transcribed, amplified by PCR, and analyzed by Southern hybridization.

Expression of the PRLR and GHR genes was detected in Southern analysis performed on PCR products of human PRLR an GHR in two human colonic adenocarcinoma cell lines HT-29 and Caco-2 at various stages of growth and differentiation. In HT-29 cells, clear signals for PRLR transcript were seen in the parental undifferentiated cells as well as in mucin-secreting variants HT-29-SB6, HT-29-MTX, and HT-29-5FU cells cultured in the presence of serum. This was also the case in the Caco-2 cells at the exponential phase of growth and in the mature Caco-2 enterocytes. Surprisingly, in addition to the band of expected size of human PRLR, 647 base pairs (bp), at least two other signals were observed in these cell lines after Southern hybridization. These additional products were subsequently purified and subcloned, and the sequences were identified (see below).

Accumulation of the GHR transcripts increased in mucin-secreting HT-29 cells compared with the parental cell line whereas the GHR transcripts were equally observed in Caco-2 cells. The results suggest that the expression of GHR gene is regulated differently during the course of growth and differentiation. As it is known that there is an isoform of human GHR that lacks exon 3 (GHRd3), two bands of PCR product or GHR transcripts (400 and 344 bp) were observed in Caco-2 and HT-29 cell lines. When a probe specific for the sequence of exon 3 of human GHR (HG 16) was used, only the band of 400 bp was seen, indicating that GHR transcript missing exon 3 is also expressed with the full-length receptor transcript in these cell lines.

Southern analysis of PCR products of PRLR and GHR transcripts in normal human and rat normal intestine were performed. In human intestine, three bands of human PRLR amplicon were detected in epithelial crypts and villi isolated from the duodenum, duodenal mucosa, and isolated colonic crypts. In the duodenum, expression was high in epithelia, lower in mucosa, and much weaker in the intestinal wall containing the muscle layers. This weak expression may explain why only two bands were detected in the duodenal wall. In the rat, both short- and long-form transcripts of PRLR were almost equally observed in the adult rat, whereas stronger signal was observed for the long-form transcript in the fetal small intestine on day 21 of gestation. Strong signals were detected in crypts and villi purified from the jejunum and ileum. Expression of PRLR gene in the colon was lower than in the upper segments of the rat intestine and transcripts of PRL and its receptor were clearly detected in the intraepithelial lymphocytes purified from the mouse small intestine.

With respect to GHR gene expression in normal human intestine, two sizes of human GHR amplicon were observed in the normal human duodenum and colon, although the band of GHRd3 (344 bp) showed weaker signals. Only the signals for the full-length GHR transcript were observed when the probe specific for exon 3 was used. For GHR expression in the rat intestine, the ileum showed a more intense signal than other parts of the GI tract. As seen for PRLR, strong signals were equally observed in small intestinal villi and crypts, suggesting that PRLR and GHR genes are expressed both in proliferative and differentiated compartments of small intestinal epithelia. In addition, two bands of PCR products were observed (452 and 320 bp) in the rat fetal intestine. Because the band of 452 bp corresponds to the expected size, the amiplicon of smaller size might be an unknown fetal-specific isoform of rat GHR. Similar variations in the molecular forms, glycosylation, and function of rat membrane receptors for peptide hormones, such as receptors for vasoactive intestinal peptide and cholecystokinin/gastrin in rats, were previously observed during the ontogenic development in the GI tract and pancreas (Chastre et al., 1987, supra).

To characterize the expression of PRLR and GHR genes in human gastrointestinal tumors, samples from colorectal and gastric tumor patients and gastric cancer cell lines were examined by Southern analysis of PCR products of PRLR and GHR transcripts. The PRLR transcript was widely observed among the samples tested, including adenomas, adenocarcinomas, and control tissue specimens from the same patients. Again, three bands of PRLR PCR products were detected by Southern analysis except for some samples, where only two bands were observed, probably due to the lower level of expression of the gene. No signal was seen in a colonic adenocarcinoma Dukes' B, although an amplicon of the cyclophilin was clearly seen and the control sample from the same patient showed clear signals.

GHR transcript was also observed widely. Interestingly, the signals for GHRd3 (344 bp) transcripts were detected more intensely than those for the full-length (400 bp) transcript in the cancer resections as well as in the control samples. Moreover, GHR3 was the only GHR transcript observed in one gastric cancer, clonic cancer Dukes' B, C, and D and their corresponding synchronous liver metastases, although all of these signals were weak. When the probe specific for exon 3 was used, only the signals for the full-length transcripts were seen. A strong signal for GHR transcripts was detected in the human gastric cell line HGT-1 whereas none was seen in the MKN-28 and -74 cell lines and in one of the gastric cancer biopsies.

The expression of PRLR and GHR genes was also examined by Southern analysis on PCR products of PRLR and GHR transcripts in the normal mucosa and epithelial cells isolated from the stomach of the human, rabbit, and fetal rat. In isolated human gastric glands, very intense signals of three sizes of amplicon for the PRLR were observed. In this sample, two bands of human GHR amplicon (full length and GHRd3) were also clearly detected. Because the gastric gland represents a heterogeneous structure, mainly composed of acid-secreting parietal cells, pepsinogen-secreting cells, and mucous cells, these three cellular fractions were purified from the rabbit gastric fundus after collagenase dispersion and elutriation centrifugation (Choquet et aI., 1993, supra). Intense signal for PRLR transcript was seen in antral mucosa and the fundic mucosal cell fraction F1 mucous cells. A moderate signal was seen in F2 chief cells and F3 parietal cells fractions, whereas the signal was very weak in muscularis mucosae. In contrast, GHR transcript was seen in all preparations from rabbit stomach, with quite similar intensity. The gastric gland isolated from fetal rats on day 21 of gestation expressed both short- and long-form transcripts of PRLR. As seen in fetal rat small intestine, two bands of GHR transcript were detected also in the fetal gastric glands.

Effect of PRL and GH on mucin and acid secretions. The secretion of the gastric M1 mucins was not statistically increased by PRL or GH (1–316 ng/ml) in HT-29-MTX cells cultured under standard conditions on petri dishes, during a 30-min to 3-h incubation period at 37° C. As a positive control carbamylcholine ($10^{-4}$ M) increased mucin secretion twofold.

Figure 3:
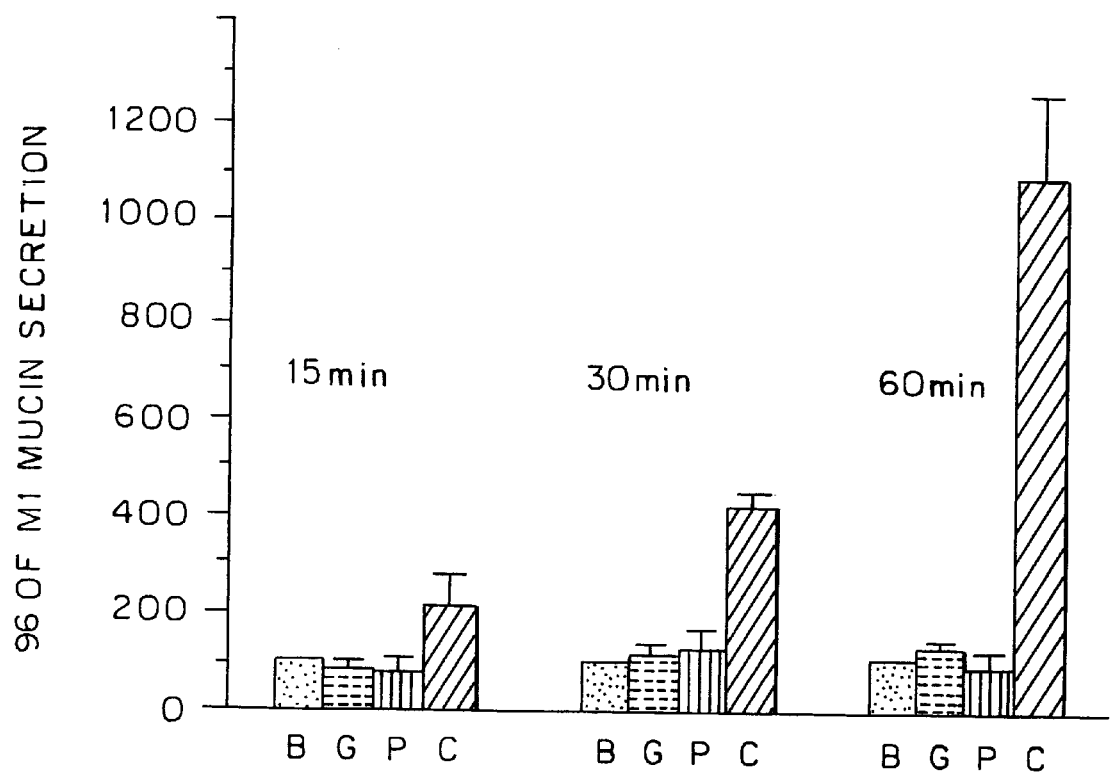
FIG. 3 shows effects of PRL, GH, and carbamylcholine on gastric M1 mucin secretion from HT-29-MTX cells cultured on polycarbonate filters. Prolactin (P, 100 ng/ml), growth hormone (G. 100 ng/ml), or carbamylcholine (C, $10^{-4}$M) were added at 37° C. from the lower compartment of Costar Transwell plates. Results were compared with untreated control cells (B). Mucin secretion was determined at the time indicated on HT-29-MTX supernatants, as indicated in the MATERIALS AND METHODS section of Example 1. Data are from two experiments. Basal levels of gastric M1 mucin secretion in untreated control cells performed in triplicate were (means±SE) 143.6±16, 145±15, and 203±20M1 AU/ml at 15, 30, and 60 min incubation, respectively.

Because these regulatory agents act on membrane receptors localized at the basolateral side of the intestinal epithelial cells, the absence of response might be related to cell differentiation and polarization. However, similar results were observed when the cells were cultured on polycarbonate filters and treated with PRL or GH, from their basolateral surface (FIG. 3). In contrast, the stimulation of gastric M1 mucin secretion by $10^{-4}$ M carbamylcholine was much higher (12-fold at 60 min) under these experimental conditions. Similarly, PRL and GH failed to increase gastric M1 mucin secretion in the F1 cell fraction containing 80% rabbit gastric mucous cells.

The effect of PRL an acid secretion was evaluated by measuring [$^{14}$C] AP accumulation in isolated rabbit parietal cells in fraction F3. PRL has no effect on AP accumulation when tested alone or in combination with the acid-secreting agents carbamylcholine or histamine.

Figure 4A:
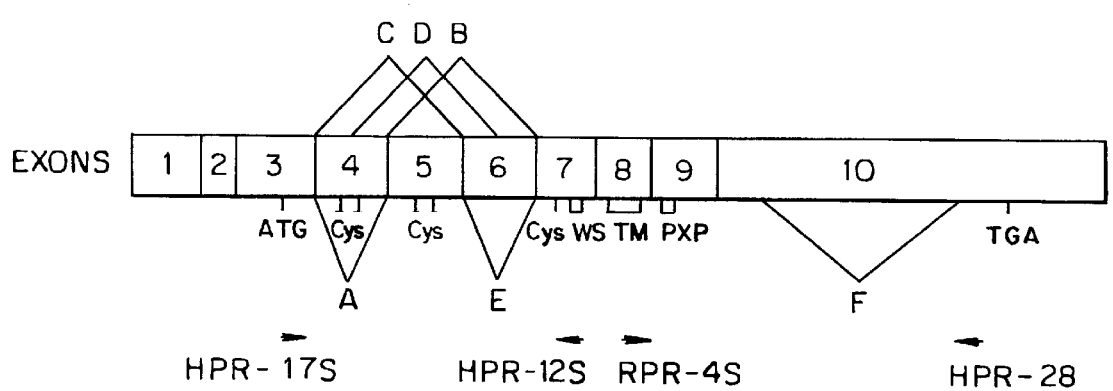
FIG. 4 is a characterization of human PRLR isoforms (clones A–F) with the positions of the deletions in the corresponding clones and the primers being shown in the schematic presentation of human PRLR cDNA relative to a start codon (ATG), a stop codon (TGA) and exons 1–10. Cys represents cysteine; WS represents a tryptophan-serine motif; TM represents transmembrane domain; and PXP represents a proline-rich region. The characteristics of the PRLR isoforms are indicated in the column below the schematic presentation for each of clones A–F. The cysteine column indicates which Cysteines (C) are retained in the protein. The sugar column indicates the number of NH$_2$-linked glycosylation site(s) (N) in the protein. Parentheses in cysteine and sugar columns represent component missing but recreate by deletion.

Isolation and characterization of human PRLR isoforms. During the analysis of the expression of PRLR gene in the human GI tract, at least two additional bands were detected in both normal and tumor tissues as well as in cell lines by Southern analysis. The PCR products from the T-47D human breast cancer cell line and normal human liver also showed the same results. RT-PCR products visualized by ethidium bromide staining in 1.5% agarose gel showed one band with the expected size and four other bands that were smaller in size than the expected band. Each band was subsequently purified, subcloned, and the sequence of these additional PCR products identified. Five clones were isolated and characterized from Caco-2 and T-47D cells. Interestingly, they were all deletion mutants, and four clones lacked precisely one or two exons. As shown in FIG. 4 clone A lacks exon 4; clone B, exons 5 and 6; clone C exons 4 and 5; clone D, exon 5 and parts of exons 4 and 6, and clone E, exon 6. The sequences surrounding deletion sites are shown in FIG. 5. Except for clone C, the deletion in all other clones resulted in a frameshift and produced a stop codon before the transmembrane domain. Thus putative protein products of these clones could be secreted forms of human PRLR. The clone E was somewhat unique: this clone conserved four cysteines, which are crucial for ligand binding (Kelly et al., 1993, supra), although it lacked the tryptophan-serine-X-tryptophan-serine motif (WS motif, where X corresponds to any amino acids), deletion of which decreases significantly the ligand binding affinity (Kelly et al., 1993, supra). In addition, the fifth cysteine was originally removed but regenerated by the frameshift. On the other hand, clone C lacked the first four cysteines but conserved the fifth cysteine and the WS motif. Because the frameshift does not occur in this clone, this isoform could be a membrane-anchored form missing a ligand binding domain but retaining one cysteine and the WS motif in the membrane-proximal region of the extracellular domain of human PRLR.

The intracellular domain of human PRLR was also examined in Caco-2 and T-47D cells as well as in normal human liver, using two oligonucleotide primers, RPR-4S and HPR-28 (FIG. 4). PCR products from all samples showed one additional band, and this amplicon was characterized in Caco-2 and T-47D cell lines. Again, this clone (clone F) was an isoform with deletion, lacking a large part of the intracellular domain (FIGS. 3 and 4). A frameshift also occurred in this clone and resulted in a short cytoplasmic tail of the putative protein. The size of the intracellular domain of the putative protein, 91 amino acids (aa), would be between rat PRLR short form (56 aa) and the intermediate form of PRLR in the Nb2 rat pre-T cell line (158 aa) (Kelly et al., 1993, supra). An interesting characteristic of clone F is that the location and size of deletion is very similar to those of the intermediate form of rat PRLR in the Nb2 cell line.

Discussion

The present study demonstrates the expression of PRLR and GHR genes in the human, rabbit, and rat GI tracts and provides the first evidence that the human GHRd3 isoform has a naturally by alternative splicing were also detected not only in normal or neoplastic tissues of the human gastrointestinal tract but also in the liver and in breast cancer cells. Expression of the two genes was mostly associated with epithelial cell populations in the normal tissues and was also observed throughout the cancerous progression of the colonic and gastric mucosa, including adenomas and liver metastases.

Expression of PRLR and GHR genes and biological function of PRL and GHR in the GI tract. In humans and rats, PRLR and GHR transcripts were preferentially localized in crypts or villi of intestine, compared with the mucosa and muscularis mucosae. Small intestinal and colonic crypts originate from a single active multipotent stem cell, and these epithelial cells undergo very active proliferation, differentiation, and migration toward the apical surface. Because PRL is known to induce ornithine decarboxylase in several tissues of the rat (Kelly et al., 1993, supra and references therein) and to stimulate GI mucosal cell proliferation in lactating rats (Kagnoff et al., *Gastroenterology*

105: 1275–1280, 1993), this preferential expression suggests that PRL could be implicated in the molecular and genetic mechanisms regulating growth and proliferation of normal and neoplastic epithelial cells in the GI tract, through polyamine synthesis. Strong expression of the PRLR mRNA was previously detected in rat Paneth cells (Oubtit et al., *Gastrointest. Liver Physiol.* 29: G807–G815, 1994), although no GHR immunoreactivity was observed in this cell type by immuno-histochemistry (Lobie et al., *Endocrinology* 126: 299–306, 1990). In the small intestine, Paneth cells located to the base of Crypt stem cells are a significant exocrine source of antimicrobial peptides and immunoregulatory agents related to host defense, since they express lysozyme and tumor necrosis factor transcripts (Kagnoff et al., 1993, supra; Keshav et al., *J. Exp. Med.* 171: 327–332, 1990; Ouellette et al., *J. Cell. Biol.* 108: 1687–1695). In the present study, clear expression of PRL and PRLR genes was demonstrated in intraepithelial lymphocytes collected from the mouse small intestine. It is well known that PRL plays important roles in the immune system, such as the restoration of immune function in hypophysectomized rats, proliferation of lymphocytes from spleens or lymph nodes of ovariectomized rats, and increase in cytotoxic activities of natural killer cells (Kelly et al., 1993, supra). In adult mice, the intestinal intraepithelial lymphocyte pool is almost comparable in size to the total peripheral T cell pool, including spleen and all lymph nodes, and consists of both $\alpha\beta$-and $\gamma\sigma$-T cell antigen receptor-positive cells. Taken together, these molecular and cellular elements suggest that PRL and PRLR may exert autocrine and/or paracrine regulations on immunologic functions in the intestinal tract, which is one of the first immunologic barriers against foreign pathogens (Kagnoff et al., 1993, supra).

Intense PRLR signals were observed in the rat duodenum, jejunum, and ileum, whereas much weaker expression was observed in the colon. The study of rabbit PRLR expression in the GI tract by Dusanter-Fourt et al. (*Endocrinology* 130: 2877–2882, 1992), using Northern analysis and radioligand binding studies, showed that the receptor in intestinal epithelial cells has a very high affinity, and its gene expression and the number of binding sites are highest in duodenal and jejunal epithelium and low in colon. Our results, which show that the small intestine is the major site of PRLR gene expression in the rat, correspond well with this previous report and also with the observation that PRL acts to water and electrolyte transport in the small intestine, whereas the colon is not responsive to the hormone (Dusanter-Fourt et al., 1992, supra and references therein). Furthermore, a recent study of PRLR expression in rabbit GI tract by immunohistochemistry has demonstrated that the most intense immunoreactivity is associated with surface epithelial cells of the duodenum and jejunum and chief cells of the fundic mucosa, as well as the esophageal epithelium and Langerhans islets (Lobie et al., *J. Endocrinol.* 139: 371–382, 1993). Thus, all these observations suggest that PRL may preferentially act on the upper segments of the GI tract.

PRLR and GHR transcripts were characterized in human gastric glands as well. To investigate the expression of these receptor genes in specific cell populations in gastric mucosa, several enriched fractions were prepared from rabbit stomach. A relatively similar level of expression was clearly detected for GHR among the fractions prepared (mucous-secreting, chief, and parietal cell fractions). And in situ hybridization study has recently indicated that human GHR transcripts are present in the stomach and the small intestine including some mucus-secreting cells (Delehaye-Zervas et al., *J. Clin. Endocrinol. Metab.* 78: 1473–1480, 1994). Lobie et al., 1990, supra have demonstrated by immunohistochemistry that rat GHR immuunoreactivity is observed in epithelial cell subpopulations of GI mucosa. They also detected GHR immunoreactivity in oligomucous and goblet cells of the rat duodenum and jejunum. However, in the same study, GHR immunoreactivity was generally not observed in well-differentiated mucus-secreting cells of the GI tract, including such cells at the base of the cardiac and pyloric glands. The sensitivity of the method and preparation of the samples (whole tissue section) could explain these differences. In contrast to what was seen for the GHR gene expression in the present study, marked differences in the level of PRLR transcripts were observed among the fractions prepared. The strong signals of PRLR transcripts in the antrum and the F1 fraction containing 80% mucous cells suggest that the receptor is intensely expressed in these exocrine cells. Clear signals were also observed in F2 and F3 fractions, representing 40–45% pepsinogen-secreting chief cells and 65–70% acid-secreting parietal cells, respectively. Expression of the PRL and GH receptor transcripts in 90–95% pure rabbit parietal cells was confirmed, using the Nycodenz gradient density method (Choquet et al., 1993, supra), suggesting that the positive signal in fraction F3 is not due to contamination of other cell types.

In rabbit parietal cell fractions, both PRL and GH did not exert a regulatory role on basal and stimulated acid secretion in the present study, suggesting that the protective action of GH on gastric ulcers (Winawer et al., 1975, supra) in not related to inhibition of acid secretion. Because PRL is well known to stimulate mucin secretion in lower vertebrates, attempts in the present study to investigate the biological functions of PRL and GH in the GI tract were conducted on the F1 rabbit gastric cell fraction and human colonic cells (HT-29-MTX). Under the conditions used in the present study, PRL or GH did not stimulate gastric M1 mucin secretion, whereas carbamylcholine stimulated a fast exocytosis of gastric M1 1 mucins from HT-29-MTX cells by rapid (5–30 min) tandem fusion of apical mucous granule membranes with the plasma membrane. In this connection, Leatherland et al., *Can. J. Zool.* 47: 787–792 (1962), observed a significant effect of PRL on the density of mucous cells on the gill filaments of sticklebacks after 6 days of PRL treatment, suggesting a long-term effect of the hormone on the proliferation differentiation balance in this cell type.

The biological roles of GH and PRL during neonatal life are also poorly understood, although GH was, reported to influence the growth of rat fetal intestinal transplants (Cooke et al., 1986, supra). In the present study, transcripts, for PRLR and GHR were clearly detected in small intestinal epithelia and gastric glands isolated from rat fetuses. It has recently been reported that rat placental lactogen II circulates in fetal serum in late pregnancy and binds specifically to the small intestinal mucosa (Freemark et al., *Endocrinology* 133: 1830–1842, 1993). Furthermore, the binding of rat placental lactogen II to fetal tissues is blocked by rat PRL as well as rat placental lactogen II, but not by rat GH, suggesting that rat placental lactogen II binding sites are closely related or identical to the PRLR (Freemark et al., 1993, supra). As reviewed recently, it is well documented that PRL, GH, and their binding proteins exist in the milks and that PRL transferred from milk to the blood circulation influences neuroendocrine development and modulation of immune functions in several species (Grosvenor et al., 1992, supra; Kelly et al., 1993, supra). Thus PRL and GH may exert their functions in the GI tract during the fetal and postnatal life.

Interestingly, GHRd3 lacking exon 3 of human GHR was also broadly expressed, and increased levels of this transcript were observed compared with full-length GHR mRNA in samples from colon and gastric adenocarcinoma patients, including the normal control sections. Moreover, GHRd3 was the only GHR transcript detected in two preparations from colorectal cancer patients that was associated with synchronous metastasis in the liver and one primary gastric cancer. The same results were also seen in two colonic adenocarcinomas without distant metastasis (Dukes B and C), even though control sections of these cancer samples expressed both forms of GHR. The functional characteristics of GHRd3 are unknown, but some data concerning its expression have been reported recently. Human GHRd3 is expressed alone or with full-length receptor in placental villi, fetal and adult normal liver, and hepatocarcinomas, as well as in IM-9 (lymphocytes) and Hep 3B (hepatoma) cell lines (Esposito et al., *Mol. Cell. Endocrinol.* 103: 13–20, 1994; Urbanek et al., 1993, supra, and references therein). The protein product of this GHR isoform is correctly expressed on the cell surface and is capable of binding GH with the same affinity as the wild type (Urbanek et al., 1993, supra). Although no relationship between GHRd3 expression and pathological characteristics has been observed (Esposito et al., 1994, supra), results of the present study suggest that GHRd3 may be responsible for mediating the biological effects of GH in normal and neoplastic epithelial cells.

Isoforms of human PRLR. Receptors for PRL and GH are members of the cytokine receptor superfamily (Kelly et al., 1993, supra). The common features of the members of this superfamily are two pairs of cysteines and the WS motif in the extracellular domain. In the case of PRLR, there are five cysteines in the extracellular domain, and the two pairs of cysteines and the WS motif have been shown to be important for the ligand binding. If one of the four cysteines is mutated to serine, the receptor loses the binding activity completely, whereas alanine substitutions of the WS motif decreases the affinity by approximately 20-fold (Kelly et al., 1993, supra).

In the present study, six isoforms of human PRLR that have a deletion in the extra- or intracellular domain were isolated. The isoforms are thought to be generated by alternative splicing, since four clones (clones A, B, C, and E) precisely lack one or two exons. Such isoforms generated by alternative splicing have also been reported for the receptors for interleukins 4, 5, 7, and 9, granulocyte macrophage-colony stimulating factor, granulocyte-colony stimulating factor, and leukemia inihibitory actor. Although the PRLR isoform transcripts were all minor products compared with the full-length receptor, the isoforms were detected not only in the GI tract but also in the liver and T-47D breast cancer cells. Some of the isoforms showed interesting characteristics (FIG. 4). Clone E would encode a secreted protein or a prolactin-binding protein (PRL-BP), which has a lower affinity for prolactin than the wild-type receptor, due to the lack of the WS motif (Kelly et al., 1993, supra). In this regard, it is of interest that clone E was expressed in T-47D human breast cancer cells. Also, clone E retains the fifth cysteine. The fifth cysteine (cysteine 184) in the wild-type PRLR has been reported not to affect the binding affinity and the biological activity of the full-length receptor (Lesueur et al., *Mol. Endocrinol.* 7: 1178–1184, 1993). However, the study by Lesueur et al., 1993, supra suggested that the PPL-BP may bind to the membrane-anchored PRLR mediated by the fifth cysteine and activate the signal transduction mechanism of PRL. In this regard, clone C is of interest, because this clone would be a membrane anchored PRLR lacking ligand binding activity but retaining the fifth cysteine and the WS motif. In contrast to human GHR, short or secreted forms of human PRLR have not been identified. However, recently identified PRL-BP from human milk were observed to have a much smaller size than the extracellular domain of human PRLR and approximately 10 to 20-fold lower affinity than that of the wild-type receptor.

Clone F lacks a large part of the intracellular domain. The position of deletion is between amino acids 312 and 503 (192 aa). The PRLR in the Nb2 cell line lacks 198 aa (aa 323–520) of the intracellular domain of the long form of rat PRLR and shows approximately threefold greater affinity. Similarities in the size and position of deletions between clone F and the N2 form of the rat PRLR suggest that these sequences constitute a hot spot of deletion or splicing. A frameshift occurs in this clone, resulting in a highly hydrophilic COOH-terminal tail that differs from the wild-type sequence.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way are admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present, invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A recombinant DNA molecule comprising a DNA segment encoding a signal peptide joined translationally in frame to a DNA segment encoding a soluble human prolactin receptor, wherein said soluble human prolactin receptor has a sequence selected from the group consisting of residues 24 to 34 of SEQ ID NO:2, residues 25 to 118 of SEQ ID NO:4, residues 25 to 48 of SEQ ID NO:6, and residues 25 to 134 of SEQ ID NO:8.

2. A recombinant DNA molecule in accordance with claim 1, wherein said soluble human prolactin receptor is capable of binding to human growth hormone as a human growth hormone-binding protein.

3. A recombinant DNA molecule in accordance with claim 1, wherein said soluble human prolactin receptor comprises amino acid residues 24 to 34 of SEQ ID NO:2.

4. A recombinant DNA molecule in accordance with claim 1, wherein said soluble human prolactin receptor comprises amino acid residues 25 to 118 of SEQ ID NO: 4.

5. A recombinant DNA molecule in accordance with claim 1, wherein said soluble human prolactin receptor comprises amino acid residues 25 to 48 of SEQ ID No:6.

6. A recombinant DNA molecule in accordance with claim 1, wherein said soluble human prolactin receptor comprises amino acid residues 25 to 134 of SEQ ID NO:8.

7. A recombinant DNA molecule in accordance with claim 1, comprising the nucleic acid sequence of SEQ ID NO:1.

8. A recombinant DNA molecule in accordance with claim 1, comprising the nucleic acid sequence of SEQ ID NO:3.

9. A recombinant DNA molecule in accordance with claim 1, comprising the nucleic acid sequence of SEQ ID NO:5.

10. A recombinant DNA molecule in accordance with claim 1, comprising the nucleic acid sequence of SEQ ID NO:7.

11. A recombinant DNA molecule in accordance with claim 1, which is an expression vector.

12. A host cell capable of expressing a soluble human prolactin receptor, wherein said host cell is transformed with an expression vector in accordance with claim 11.

13. A method of producing a soluble human prolactin receptor, comprising the steps of:

culturing the host cell of claim 12 in a nutrient medium to express and produce said soluble human prolactin receptor; and recovering said produced soluble human prolactin receptor.

14. The recombinant DNA molecule according to claim 1, wherein the soluble human prolactin receptor naturally occurs in the human intestine.

15. A recombinant DNA molecule comprising a DNA segment encoding a signal peptide joined transitionally in frame to a DNA segment encoding a polypeptide comprising residues 25 to 349 of SEQ ID NO:14.

16. A recombinant DNA molecule in accordance with claim 15, which is an expression vector.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 105 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..102

(xi) SEQUENCE DESCRIPTION: SEQ ID NO:1:

```
ATG AAG GAA AAT GTG GCA TCT GCA ACC GTT TTC ACT CTG CTA CTT TTT      48
Met Lys Glu Asn Val Ala Ser Ala Thr Val Phe Thr Leu Leu Leu Phe
 1               5                  10                  15

CTC AAC ACC TGC CTT CTG AAT GAG AGA CAC TCA TGC ATG AAT GTC CAG      96
Leu Asn Thr Cys Leu Leu Asn Glu Arg His Ser Cys Met Asn Val Gln
             20                  25                  30

ACT ACA TAA                                                         105
Thr Thr
```

(2) INFORMATION FOR SEQ ID NO:2:

(i) SEQUENCE CHARACTERISTICS:
      (A) LENGTH: 34 amino acids
      (B) TYPE: amino acid
      (D) TOPOLOGY: linear (ii) MOLECULE TYPE: protein (xi) SEQUENCE DESCRIPTION: SEQ ID NO:2:

```
Met Lys Glu Asn Val Ala Ser Ala Thr Val Phe Thr Leu Leu Leu Phe
 1               5                  10                  15

Leu Asn Thr Cys Leu Leu Asn Glu Arg His Ser Cys Met Asn Val Gln
             20                  25                  30

Thr Thr
```

(2) INFORMATION FOR SEQ ID NO:3:

(i) SEQUENCE CHARACTERISTICS:
      (A) LENGTH: 357 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..354

(xi) SEQUENCE DESCRIPTION: SEQ ID NO:3:

```
ATG AAG GAA AAT GTG GCA TCT GCA ACC GTT TTC ACT CTG CTA CTT TTT      48
Met Lys Glu Asn Val Ala Ser Ala Thr Val Phe Thr Leu Leu Leu Phe
 1               5                  10                  15

CTC AAC ACC TGC CTT CTG AAT GGA CAG TTA CCT CCT GGA AAA CCT GAG      96
Leu Asn Thr Cys Leu Leu Asn Gly Gln Leu Pro Pro Gly Lys Pro Glu
             20                  25                  30
```

```
ATC TTT AAA TGT CGT TCT CCC AAT AAG GAA ACA TTC ACC TGC TGG TGG    144
Ile Phe Lys Cys Arg Ser Pro Asn Lys Glu Thr Phe Thr Cys Trp Trp
        35                  40                  45

AGG CCT GGG ACA GAT GGA GGA CTT CCT ACC AAT TAT TCA CTG ACT TAC    192
Arg Pro Gly Thr Asp Gly Gly Leu Pro Thr Asn Tyr Ser Leu Thr Tyr
    50                  55                  60

CAC AGG GAA GGA TCC ATT TTG CTG GGC AGC AAA CAG AGT TTA AGA TTC    240
His Arg Glu Gly Ser Ile Leu Leu Gly Ser Lys Gln Ser Leu Arg Phe
65                  70                  75                  80

TCA GCC TAC ATC CAG GAC AGA AAT ACC TTG TCC AGG TTC GCT GCA AAC    336
Ser Ala Tyr Ile Gln Asp Arg Asn Thr Leu Ser Arg Phe Ala Ala Asn
                85                  90                  95

CAG ACC ATG GAT ACT GGA GTG CAT GGA GTC CAG CGA CCT TCA TTC AGA    336
Gln Thr Met Asp Thr Gly Val His Gly Val Gln Arg Pro Ser Phe Arg
            100                 105                 110

TAC CTA GTG ACT TCA CCA TGA                                        357
Tyr Leu Val Thr Ser Pro
        115

(2) INFORMATION FOR SEQ ID NO:4:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO:4:

Met Lys Glu Asn Val Ala Ser Ala Thr Val Phe Thr Leu Leu Leu Phe
 1               5                  10                  15

Leu Asn Thr Cys Leu Leu Asn Gly Gln Leu Pro Pro Gly Lys Pro Glu
            20                  25                  30

Ile Phe Lys Cys Arg Ser Pro Asn Lys Glu Thr Phe Thr Cys Trp Trp
        35                  40                  45

Arg Pro Gly Thr Asp Gly Gly Leu Pro Thr Asn Tyr Ser Leu Thr Tyr
    50                  55                  60

His Arg Glu Gly Ser Ile Leu Leu Gly Ser Lys Gln Ser Leu Arg Phe
65                  70                  75                  80

Ser Ala Tyr Ile Gln Asp Arg Asn Thr Leu Ser Arg Phe Ala Ala Asn
                85                  90                  95

Gln Thr Met Asp Thr Gly Val His Gly Val Gln Arg Pro Ser Phe Arg
            100                 105                 110

Tyr Leu Val Thr Ser Pro
        115

(2) INFORMATION FOR SEQ ID NO:5:

(i) SEQUENCE CHARACTERISTICS:
        (A) LENGTH: 147 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..144

(xi) SEQUENCE DESCRIPTION: SEQ ID NO:5:

ATG AAG GAA AAT GTG GCA TCT GCA ACC GTT TTC ACT CTG CTA CTT TTT     48
```

```
Met Lys Glu Asn Val Ala Ser Ala Thr Val Phe Thr Leu Leu Leu Phe
  1               5                  10                  15

CTC AAC ACC TGC CTT CTG AAT GGA CAG TTA CCT CCT GGA AAA CCT GAG         96
Leu Asn Thr Cys Leu Leu Asn Gly Gln Leu Pro Pro Gly Lys Pro Glu
                 20                  25                  30

ATC TTT AAA TGT CGT TCT CCC AAT AAG GAA ACA TTC ACC TAC CCT GAT        144
Ile Phe Lys Cys Arg Ser Pro Asn Lys Glu Thr Phe Thr Tyr Pro Asp
             35                  40                  45

TGA                                                                    147
```

(2) INFORMATION FOR SEQ ID NO:6:

(i) SEQUENCE CHARACTERISTICS:
        (A) LENGTH: 48 amino acids
        (B) TYPE: amino acid
        (D) TOPOLOGY: linear (ii) MOLECULE TYPE: protein (xi) SEQUENCE DESCRIPTION: SEQ ID NO:6:

```
Met Lys Glu Asn Val Ala Ser Ala Thr Val Phe Thr Leu Leu Leu Phe
  1               5                  10                  15

Leu Asn Thr Cys Leu Leu Asn Gly Gln Leu Pro Pro Gly Lys Pro Glu
                 20                  25                  30

Ile Phe Lys Cys Arg Ser Pro Asn Lys Glu Thr Phe Thr Tyr Pro Asp
             35                  40                  45
```

(2) INFORMATION FOR SEQ ID NO:7:

(i) SEQUENCE CHARACTERISTICS:
        (A) LENGTH: 405 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..402

(xi) SEQUENCE DESCRIPTION: SEQ ID NO:7:

```
ATG AAG GAA AAT GTG GCA TCT GCA ACC GTT TTC ACT CTG CTA CTT TTT         48
Met Lys Glu Asn Val Ala Ser Ala Thr Val Phe Thr Leu Leu Leu Phe
  1               5                  10                  15

CTC AAC ACC TGC CTT CTG AAT GGA CAG TTA CCT CCT GGA AAA CCT GAG         96
Leu Asn Thr Cys Leu Leu Asn Gly Gln Leu Pro Pro Gly Lys Pro Glu
                 20                  25                  30

ATC TTT AAA TGT CGT TCT CCC AAT AAG GAA ACA TTC ACC TGC TGG TGG        144
Ile Phe Lys Cys Arg Ser Pro Asn Lys Glu Thr Phe Thr Cys Trp Trp
             35                  40                  45

AGG CCT GGG ACA GAT GGA GGA CTT CCT ACC AAT TAT TCA CTG ACT TAC        192
Arg Pro Gly Thr Asp Gly Gly Leu Pro Thr Asn Tyr Ser Leu Thr Tyr
         50                  55                  60

CAC AGG GAA GGA GAG ACA CTC ATG CAT GAA TGT CCA GAC TAC ATA ACC        240
His Arg Glu Gly Glu Thr Leu Met His Glu Cys Pro Asp Tyr Ile Thr
 65                  70                  75                  80

GGT GGC CCC AAC TCC TGC CAC TTT GGC AAG CAG TAC ACC TCC ATG TGG        288
Gly Gly Pro Asn Ser Cys His Phe Gly Lys Gln Tyr Thr Ser Met Trp
                 85                  90                  95

AGG ACA TAC ATC ATG ATG GTC AAT GCC ACT AAC CAG ATG GGA AGC AGT        336
Arg Thr Tyr Ile Met Met Val Asn Ala Thr Asn Gln Met Gly Ser Ser
```

-continued

```
                    100                 105                 110
TTC TCG GAT GAA CTT TAT GTG GAC GTG ACT TAC ATA GAT CCA TTT TGC         384
Phe Ser Asp Glu Leu Tyr Val Asp Val Thr Tyr Ile Asp Pro Phe Cys
        115                 120                 125

TGG GCA GCA AAC AGA GTT TAA                                             405
Trp Ala Ala Asn Arg Val
    130
```

(2) INFORMATION FOR SEQ ID NO:8:

(i) SEQUENCE CHARACTERISTICS:
        (A) LENGTH: 134 amino acids
        (B) TYPE: amino acid
        (D) TOPOLOGY: linear (ii) MOLECULE TYPE: protein (xi) SEQUENCE DESCRIPTION: SEQ ID NO:8:

```
Met Lys Glu Asn Val Ala Ser Ala Thr Val Phe Thr Leu Leu Leu Phe
 1               5                  10                  15

Leu Asn Thr Cys Leu Leu Asn Gly Gln Leu Pro Pro Gly Lys Pro Glu
            20                  25                  30

Ile Phe Lys Cys Arg Ser Pro Asn Lys Glu Thr Phe Thr Cys Trp Trp
        35                  40                  45

Arg Pro Gly Thr Asp Gly Gly Leu Pro Thr Asn Tyr Ser Leu Thr Tyr
    50                  55                  60

His Arg Glu Gly Glu Thr Leu Met His Glu Cys Pro Asp Tyr Ile Thr
65                  70                  75                  80

Gly Gly Pro Asn Ser Cys His Phe Gly Lys Gln Tyr Thr Ser Met Trp
            85                  90                  95

Arg Thr Tyr Ile Met Met Val Asn Ala Thr Asn Gln Met Gly Ser Ser
            100                 105                 110

Phe Ser Asp Glu Leu Tyr Val Asp Val Thr Tyr Ile Asp Pro Phe Cys
        115                 120                 125

Trp Ala Ala Asn Arg Val
    130
```

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..21

(xi) SEQUENCE DESCRIPTION: SEQ ID NO:9:

```
CTT CTG AAT GTT CAG CCA GAC                                              21
Leu Leu Asn Val Gln Pro Asp
 1               5
```

(2) INFORMATION FOR SEQ ID NO:10:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:10:

Leu Leu Asn Val Gln Pro Asp
  1               5

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

CCAAGTCAAG AGAGAGAA                                                      18

(2) INFORMATION FOR SEQ ID NO:12:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Pro Ser Gln Glu Arg Glu Gln Arg Gln Ala Gln Glu Ala Arg Asp Ser
  1               5                  10                  15

(2) INFORMATION FOR SEQ ID NO:13:

(i) SEQUENCE CHARACTERISTICS:
        (A) LENGTH: 1050 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1050

(xi) SEQUENCE DESCRIPTION: SEQ ID NO:13:

```
ATG AAG GAA AAT GTG GCA TCT GCA ACC GTT TTC ACT CTG CTA CTT TTT          48
Met Lys Glu Asn Val Ala Ser Ala Thr Val Phe Thr Leu Leu Leu Phe
  1               5                  10                  15

CTC AAC ACC TGC CTT CTG AAT GGA CAG TTA CCT CCT GGA AAA CCT GAG          96
Leu Asn Thr Cys Leu Leu Asn Gly Gln Leu Pro Pro Gly Lys Pro Glu
                 20                  25                  30

ATC TTT AAA TGT CGT TCT CCC AAT AAG GAA ACA TTC ACC TGC TGG TGG         144
Ile Phe Lys Cys Arg Ser Pro Asn Lys Glu Thr Phe Thr Cys Trp Trp
             35                  40                  45

AGG CCT GGG ACA GAT GGA GGA CTT CCT ACC AAT TAT TCA CTG ACT TAC         192
Arg Pro Gly Thr Asp Gly Gly Leu Pro Thr Asn Tyr Ser Leu Thr Tyr
         50                  55                  60

CAC AGG GAA GGA GAG ACA CTC ATG CAT GAA TGT CCA GAC TAC ATA ACC         240
His Arg Glu Gly Glu Thr Leu Met His Glu Cys Pro Asp Tyr Ile Thr
 65                  70                  75                  80

GGT GGC CCC AAC TCC TGC CAC TTT GGC AAG CAG TAC ACC TCC ATG TGG         288
Gly Gly Pro Asn Ser Cys His Phe Gly Lys Gln Tyr Thr Ser Met Trp
                 85                  90                  95

AGG ACA TAC ATC ATG ATG GTC AAT GCC ACT AAC CAG ATG GGA AGC AGT         336
```

```
Arg Thr Tyr Ile Met Met Val Asn Ala Thr Asn Gln Met Gly Ser Ser
            100                 105                 110

TTC TCG GAT GAA CTT TAT GTG GAC GTG ACT TAC ATA GTT CAG CCA GAC      384
Phe Ser Asp Glu Leu Tyr Val Asp Val Thr Tyr Ile Val Gln Pro Asp
        115                 120                 125

CCT CCT TTG GAG CTG GCT GTG GAA GTA AAA CAG CCA GAA GAC AGA AAA      432
Pro Pro Leu Glu Leu Ala Val Glu Val Lys Gln Pro Glu Asp Arg Lys
130                 135                 140

CCC TAC CTG TGG ATT AAA TGG TCT CCA CCT ACC CTG ATT GAC TTA AAA      480
Pro Tyr Leu Trp Ile Lys Trp Ser Pro Pro Thr Leu Ile Asp Leu Lys
145                 150                 155                 160

ACT GGT TGG TTC ACG CTC CTG TAT GAA ATT CGA TTA AAA CCC GAG AAA      528
Thr Gly Trp Phe Thr Leu Leu Tyr Glu Ile Arg Leu Lys Pro Glu Lys
                165                 170                 175

GCA GCT GAG TGG GAG ATC CAT TTT GCT GGG CAG CAA ACA GAG TTT AAG      576
Ala Ala Glu Trp Glu Ile His Phe Ala Gly Gln Gln Thr Glu Phe Lys
                180                 185                 190

ATT CTC AGC CTA CAT CCA GGA CAG AAA TAC CTT GTC CAG GTT CGC TGC      624
Ile Leu Ser Leu His Pro Gly Gln Lys Tyr Leu Val Gln Val Arg Cys
                195                 200                 205

AAA CCA GAC CAT GGA TAC TGG AGT GCA TGG AGT CCA GCG ACC TTC ATT      672
Lys Pro Asp His Gly Tyr Trp Ser Ala Trp Ser Pro Ala Thr Phe Ile
210                 215                 220

CAG ATA CCT AGT GAC TTC ACC ATG AAT GAT ACA ACC GTG TGG ATC TCT      720
Gln Ile Pro Ser Asp Phe Thr Met Asn Asp Thr Thr Val Trp Ile Ser
225                 230                 235                 240

GTG GCT GTC CTT TCT GCT GTC ATC TGT TTG ATT ATT GTC TGG GCA GTG      768
Val Ala Val Leu Ser Ala Val Ile Cys Leu Ile Ile Val Trp Ala Val
                245                 250                 255

GCT TTG AAG GGC TAT AGC ATG GTG ACC TGC ATC TTT CCG CCA GTT CCT      816
Ala Leu Lys Gly Tyr Ser Met Val Thr Cys Ile Phe Pro Pro Val Pro
                260                 265                 270

GGG CCA AAA ATA AAA GGA TTT GAT GCT CAT CTG TTG GAG AAG GGC AAG      864
Gly Pro Lys Ile Lys Gly Phe Asp Ala His Leu Leu Glu Lys Gly Lys
                275                 280                 285

TCT GAA GAA CTA CTG AGT GCC TTG GGA TGC CAA GAC TTT CCT CCC ACT      912
Ser Glu Glu Leu Leu Ser Ala Leu Gly Cys Gln Asp Phe Pro Pro Thr
290                 295                 300

TCT GAC TAT GAG GAC TTG CTG GTG GAG TAT TTA GAA GTA GAT GAT AGT      960
Ser Asp Tyr Glu Asp Leu Leu Val Glu Tyr Leu Glu Val Asp Asp Ser
305                 310                 315                 320

GAG GAC CAG CAT CTA ATG TCA GTC CAT TCA AAA GAA CAC CCA AGT CAA     1008
Glu Asp Gln His Leu Met Ser Val His Ser Lys Glu His Pro Ser Gln
                325                 330                 335

GAG AGA GAA CAG CGG CAA GCC CAA GAA GCC CGG GAC TCC TGA             1050
Glu Arg Glu Gln Arg Gln Ala Gln Glu Ala Arg Asp Ser
                340                 345

(2) INFORMATION FOR SEQ ID NO:14:

(i) SEQUENCE CHARACTERISTICS:
        (A) LENGTH: 349 amino acids
        (B) TYPE: amino acid
        (D) TOPOLOGY: linear (ii) MOLECULE TYPE: protein (xi) SEQUENCE DESCRIPTION: SEQ ID NO:14:

Met Lys Glu Asn Val Ala Ser Ala Thr Val Phe Thr Leu Leu Phe
 1               5                  10                  15

Leu Asn Thr Cys Leu Leu Asn Gly Gln Leu Pro Pro Gly Lys Pro Glu
```

-continued

```
                    20                  25                  30
Ile Phe Lys Cys Arg Ser Pro Asn Lys Glu Thr Phe Thr Cys Trp Trp
        35                  40                  45

Arg Pro Gly Thr Asp Gly Gly Leu Pro Thr Asn Tyr Ser Leu Thr Tyr
    50                  55                  60

His Arg Glu Gly Glu Thr Leu Met His Glu Cys Pro Asp Tyr Ile Thr
65                  70                  75                  80

Gly Gly Pro Asn Ser Cys His Phe Gly Lys Gln Tyr Thr Ser Met Trp
                85                  90                  95

Arg Thr Tyr Ile Met Met Val Asn Ala Thr Asn Gln Met Gly Ser Ser
                100                 105                 110

Phe Ser Asp Glu Leu Tyr Val Asp Val Thr Tyr Ile Val Gln Pro Asp
            115                 120                 125

Pro Pro Leu Glu Leu Ala Val Glu Val Lys Gln Pro Glu Asp Arg Lys
    130                 135                 140

Pro Tyr Leu Trp Ile Lys Trp Ser Pro Pro Thr Leu Ile Asp Leu Lys
145                 150                 155                 160

Thr Gly Trp Phe Thr Leu Leu Tyr Glu Ile Arg Leu Lys Pro Glu Lys
                165                 170                 175

Ala Ala Glu Trp Glu Ile His Phe Ala Gly Gln Gln Thr Glu Phe Lys
                180                 185                 190

Ile Leu Ser Leu His Pro Gly Gln Lys Tyr Leu Val Gln Val Arg Cys
            195                 200                 205

Lys Pro Asp His Gly Tyr Trp Ser Ala Trp Ser Pro Ala Thr Phe Ile
    210                 215                 220

Gln Ile Pro Ser Asp Phe Thr Met Asn Asp Thr Thr Val Trp Ile Ser
225                 230                 235                 240

Val Ala Val Leu Ser Ala Val Ile Cys Leu Ile Ile Val Trp Ala Val
                245                 250                 255

Ala Leu Lys Gly Tyr Ser Met Val Thr Cys Ile Phe Pro Pro Val Pro
                260                 265                 270

Gly Pro Lys Ile Lys Gly Phe Asp Ala His Leu Leu Glu Lys Gly Lys
        275                 280                 285

Ser Glu Glu Leu Leu Ser Ala Leu Gly Cys Gln Asp Phe Pro Pro Thr
    290                 295                 300

Ser Asp Tyr Glu Asp Leu Leu Val Glu Tyr Leu Glu Val Asp Asp Ser
305                 310                 315                 320

Glu Asp Gln His Leu Met Ser Val His Ser Lys Glu His Pro Ser Gln
                325                 330                 335

Glu Arg Glu Gln Arg Gln Ala Gln Glu Ala Arg Asp Ser
                340                 345
```